US009600886B2

(12) United States Patent
Shimizu et al.

(10) Patent No.: US 9,600,886 B2
(45) Date of Patent: Mar. 21, 2017

(54) OPTICAL IMAGE MEASURING APPARATUS

(71) Applicant: KABUSHIKI KAISHA TOPCON, Itabashi-ku (JP)

(72) Inventors: Hitoshi Shimizu, Itabashi-ku (JP); Takashi Fujimura, Fujiminio (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 3 days.

(21) Appl. No.: 14/441,745

(22) PCT Filed: Oct. 9, 2013

(86) PCT No.: PCT/JP2013/077470
§ 371 (c)(1),
(2) Date: May 8, 2015

(87) PCT Pub. No.: WO2014/077057
PCT Pub. Date: May 22, 2014

(65) Prior Publication Data
US 2015/0294468 A1 Oct. 15, 2015

(30) Foreign Application Priority Data
Nov. 19, 2012 (JP) .................................. 2012-253281

(51) Int. Cl.
*G01B 9/02* (2006.01)
*G06T 7/00* (2006.01)
*A61B 3/10* (2006.01)

(52) U.S. Cl.
CPC ............ *G06T 7/0042* (2013.01); *A61B 3/102* (2013.01); *G01B 9/02091* (2013.01); *G06T 2207/10101* (2013.01)

(58) Field of Classification Search
CPC ............ G01B 9/02083; G01B 9/02085; G01B 9/02087

(Continued)

(56) References Cited

U.S. PATENT DOCUMENTS 6,377,349 B1 4/2002 Fercher
2007/0086011 A1 4/2007 Toida
(Continued)

FOREIGN PATENT DOCUMENTS

JP 11-325849 A 11/1999
JP 2005-111053 A 4/2005
(Continued)

OTHER PUBLICATIONS

International Search Report Issued Nov. 19, 2013 in PCT/JP13/077470 Filed Oct. 9, 2013.

*Primary Examiner* — Jonathan Hansen
(74) *Attorney, Agent, or Firm* — Oblon, McClelland, Maier & Neustadt, L.L.P.

(57) ABSTRACT

An optical image measuring apparatus including an optical system, image forming part, controller, and composite-cross-sectional-image forming part. The optical system includes a scanner changing an irradiation position of signal light on an object and a focus position changing part changing a focus position of the signal light. The optical system detects interference light of returned light of the respective signal light from the object and reference light. The image forming part forms a cross-sectional image based on detection results of plural interference light corresponding to plural irradiation positions of the signal light. The controller controls the optical system to irradiate the signal light onto the plural irradiation positions repeatedly while changing focus position. The composite-cross-sectional-image forming part forms one composite cross-sectional image based on two or more of the cross-sectional images based on results of repetitive irradiation of the signal light.

12 Claims, 18 Drawing Sheets

(58) Field of Classification Search
USPC .................................................. 356/479, 497
See application file for complete search history.

(56) References Cited

U.S. PATENT DOCUMENTS

| | | | |
|---|---|---|---|
| 2010/0149489 A1 | 6/2010 | Kikawa et al. | |
| 2011/0267340 A1* | 11/2011 | Kraus | A61B 3/102 345/419 |
| 2012/0044455 A1* | 2/2012 | Hirose | G01B 11/2441 351/206 |
| 2012/0249954 A1* | 10/2012 | Uchida | A61B 3/102 351/206 |

FOREIGN PATENT DOCUMENTS

| | | |
|---|---|---|
| JP | 2007-24677 A | 2/2007 |
| JP | 2007-101250 A | 4/2007 |
| JP | 2008-73099 A | 4/2008 |
| JP | 2008-289579 A | 12/2008 |
| JP | 2010-279681 A | 12/2010 |
| WO | 2011/139895 A1 | 11/2011 |

\* cited by examiner

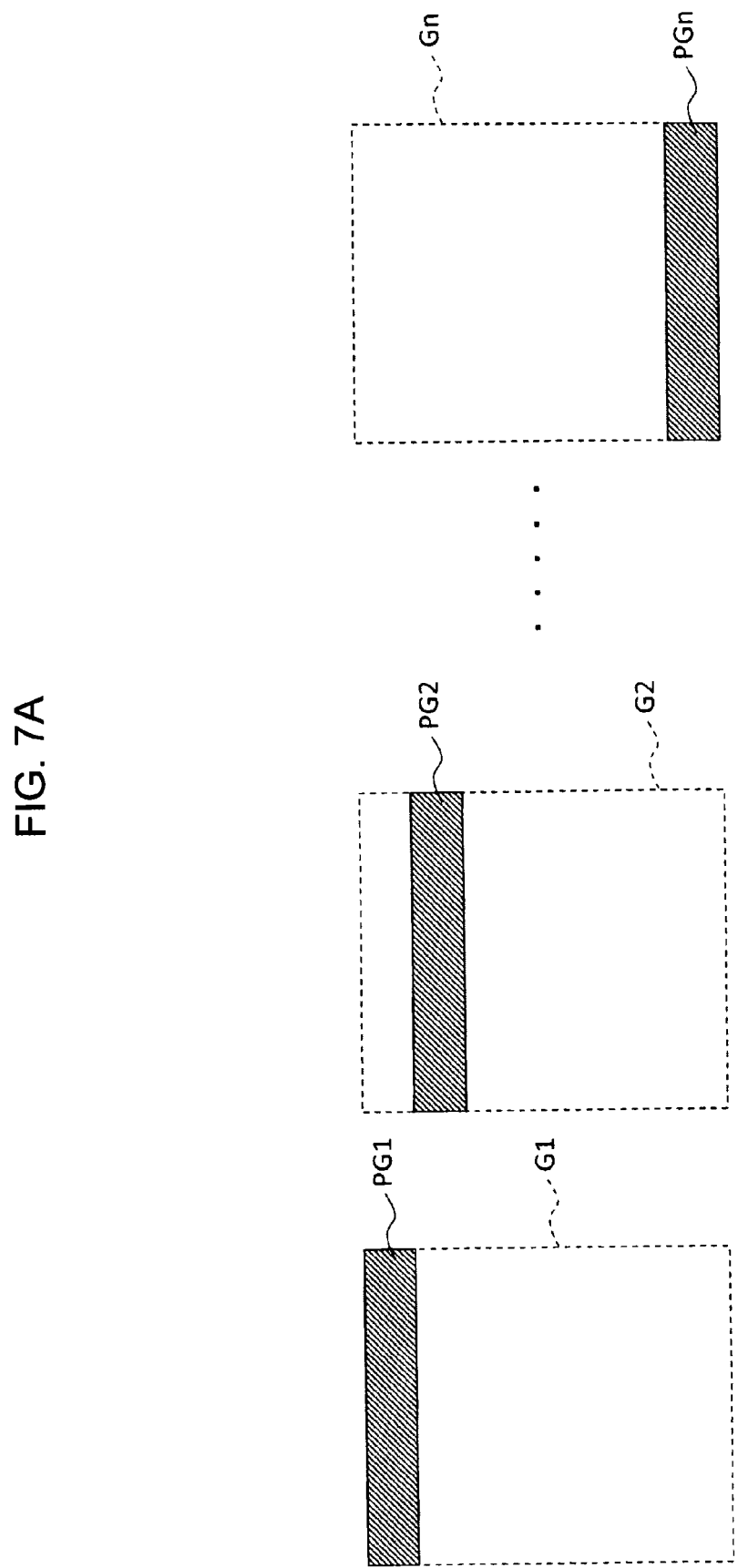

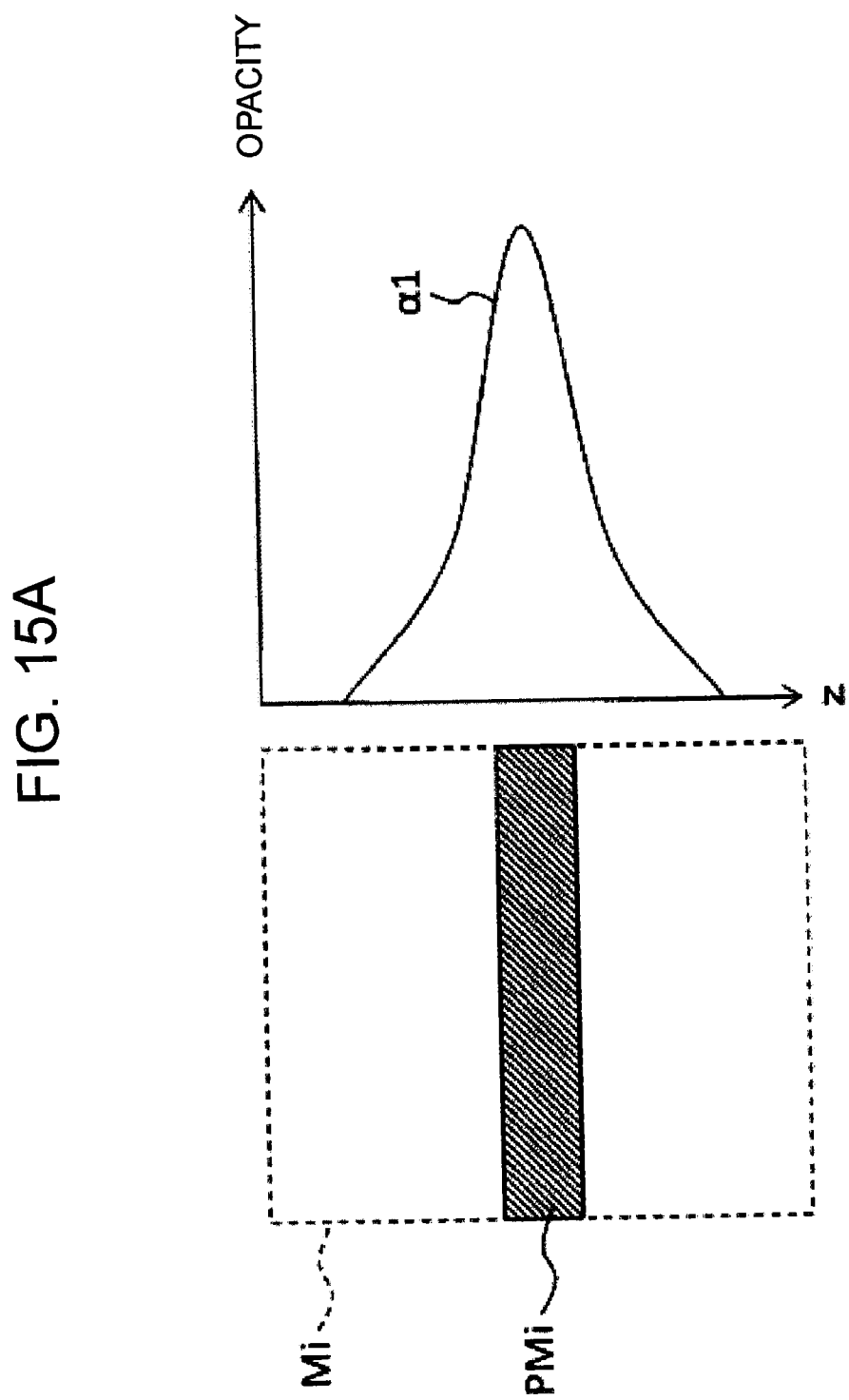

OPTICAL IMAGE MEASURING APPARATUS

CROSS-REFERENCE TO RELATED APPLICATION

This application is based upon and claims the benefit of priority from Japanese Patent Application No. 2012-253281, filed Nov. 19, 2012; the entire contents of which are incorporated herein by reference.

TECHNICAL FIELD

The present invention relates to optical image measuring technology for acquiring images of an object using optical coherence tomography (OCT).

BACKGROUND TECHNOLOGY

In recent years, OCT that forms images representing surface and/or internal morphology of objects using light beams from laser light sources etc. has attracted attention. Unlike X-ray CT, OCT is noninvasive to human bodies and is therefore expected to be utilized in medical and biological fields in particular. For example, in ophthalmology, apparatuses for forming images of fundus, cornea, etc. are in practical stages.

Patent Document 1 discloses an apparatus that uses so-called "Fourier Domain OCT" technique. Specifically, this apparatus irradiates low-coherence light beam to an object, superposes its reflected light and reference light to generate interference light, acquires spectral intensity distribution of the interference light, and executes Fourier transform on it to image morphology of the object in a depth direction (z-direction). Further, this apparatus is provided with a galvano mirror for scanning light beams (signal light) in one direction (x-direction) perpendicular to the z-direction, and forms an image of a desired measurement target region of the object. An image formed by this apparatus is a two-dimensional cross-sectional image along the depth direction (z-direction) and scanning direction (x-direction) of the light beam. Such a technique is specifically called Spectral Domain. Patent Document 2 also discloses an OCT apparatus of Spectral Domain type.

Patent Document 3 discloses an OCT apparatus that scans wavelengths of light irradiated to an object (wavelength sweeping), detects interference light obtained by superposing reflected lights of the respective wavelengths on reference light to acquire spectral intensity distribution, and executes Fourier transform on it to image morphology of the object. Such an OCT technique is called Swept Source etc. Swept Source type is a kind of Fourier Domain type. Patent Document 4 discloses a configuration in which OCT is applied to ophthalmology.

OCT apparatuses have advantages in that high-definition images may be obtained, cross-sectional and three-dimensional images may be obtained, etc.

PRIOR ART DOCUMENTS

Patent Documents

[Patent Document 1] Japanese Unexamined Patent Application Publication No. H11-325849
[Patent Document 2] Japanese Unexamined Patent Application Publication No. 2007-101250
[Patent Document 3] Japanese Unexamined Patent Application Publication No. 2007-24677
[Patent Document 4] Japanese Unexamined Patent Application Publication No. 2008-73099

SUMMARY OF THE INVENTION

Problems to be Solved by the Invention

Conventional OCT apparatuses include optical systems with large NA (numerical aperture) in order to improve lateral resolution. However, large value of numerical aperture gives shallow depth of focus, thereby easily causing bokeh (blur) in images. That is, lateral resolution and sharpness of whole image are in trade-off relationship and coexistence of these is difficult by means of conventional technology.

A purpose of the present invention is to provide technology capable of acquiring images with high lateral resolution and global sharpness.

Means for Solving the Problem

An embodiment is an optical image measuring apparatus comprising: an optical system including a scanner configured to change an irradiation position of signal light on an object and a focus position changing part configured to change focus position of the signal light, and configured to detect interference light of returned light of the respective signal light from the object and reference light; an image forming part configured to form a cross-sectional image based on detection results of a plurality of interference light corresponding to a plurality of irradiation positions of the signal light; a controller configured to control the optical system to irradiate the signal light onto the plurality of irradiation positions repeatedly while changing the focus position; a composite-cross-sectional-image forming part configured to form one composite cross-sectional image based on two or more cross-sectional images formed by the image forming part on the basis of results of repetitive irradiation of the signal light.

Effect of the Invention

According to the present invention, it is possible to acquire images with high lateral resolution and global sharpness.

BRIEF DESCRIPTION OF THE DRAWINGS

FIG. 7A is a schematic diagram for explaining a configuration of an optical image measuring apparatus (fundus observation apparatus) according to an embodiment.

FIG. 15A is a schematic diagram for explaining an operation example of an optical image measuring apparatus (fundus observation apparatus) according to a modification.

MODE FOR CARRYING OUT THE INVENTION

Examples of embodiments of optical image measuring apparatuses of the present invention are described in detail with reference to drawings. Optical image measuring apparatuses of the present invention form cross-sectional images and/or three-dimensional images of objects. In this specification, images acquired by OCT are sometimes referred to as OCT images. Further, measurement actions for forming OCT images are sometimes referred to as OCT (measurement). The contents disclosed in the documents cited in this specification may be applied to the following embodiments. Further, various configurations described in the following embodiments and modifications may be combined in arbitrary ways.

In the following embodiments, an object is assumed to be an eye (fundus), and fundus observation apparatuses that apply Fourier Domain OCT to perform OCT for a fundus are described. Particularly, fundus observation apparatuses of embodiments are capable of obtaining OCT images of a fundus by means of Spectral Domain OCT and obtaining fundus images. Configurations of the present invention may be applied to optical image measuring apparatuses of any type other than Spectral Domain (for example, Swept Source OCT). The following embodiments describe apparatuses as combinations of OCT apparatuses and retinal cameras; however, ophthalmologic imaging apparatuses other than retinal cameras (such as SLO, slit lamp microscope, ophthalmologic operation microscope, etc.) may be combined with OCT apparatuses having configurations of embodiments. Configurations of embodiments may be integrated into single-functional OCT apparatuses.

[Configurations]

Figure 1:
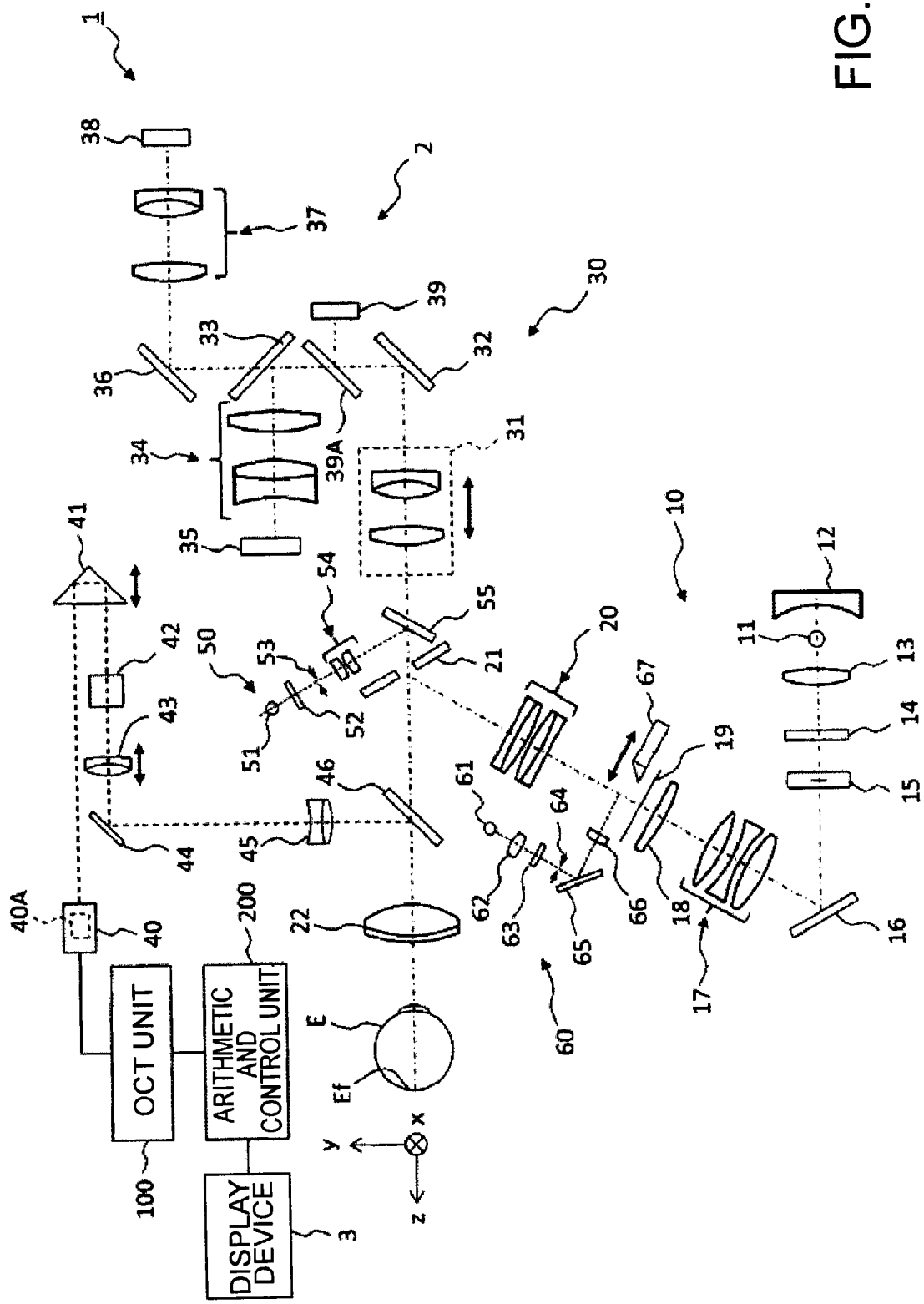
FIG. 1 is a schematic diagram illustrating a configuration example of an optical image measuring apparatus (fundus observation apparatus) according to an embodiment.
Figure 2:
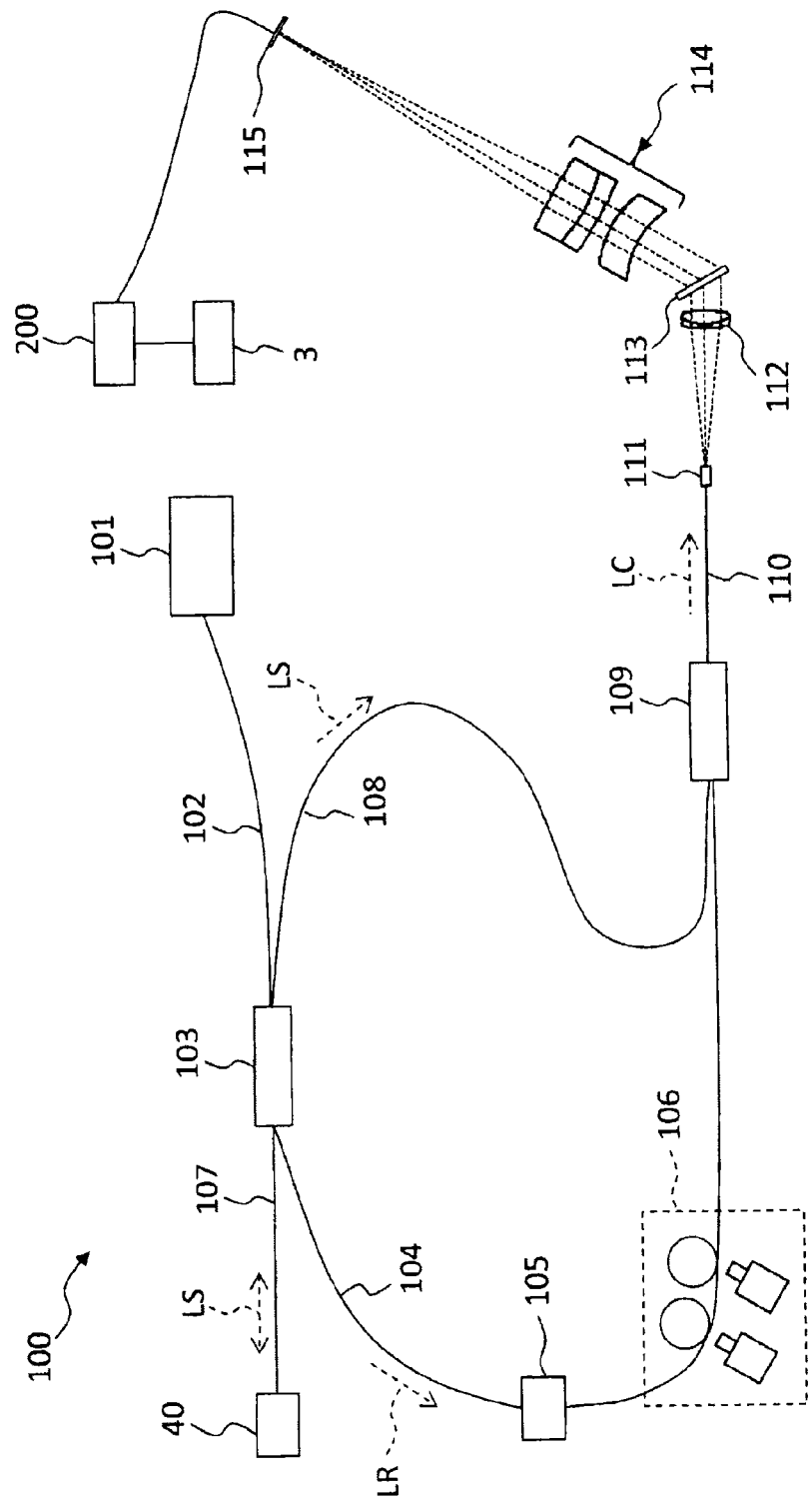
FIG. 2 is a schematic diagram illustrating a configuration example of an optical image measuring apparatus (fundus observation apparatus) according to an embodiment.

As shown in FIG. 1 and FIG. 2, a fundus observation apparatus (optical image measuring apparatus) 1 includes a retinal camera unit 2, OCT unit 100 and arithmetic and control unit 200. The retinal camera unit 2 includes almost the same optical system as a conventional retinal camera. The OCT unit 100 is provided with optical systems for obtaining fundus OCT images. The arithmetic and control unit 200 includes a computer that executes various arithmetic processing, control processing, etc.

[Retinal Camera Unit]

The retinal camera unit 2 shown in FIG. 1 is provided with optical systems for obtaining two-dimensional images (fundus images) representing surface morphology of a fundus Ef of an eye E. Fundus images include observation images, photographed images, etc. The observation image is, for example, a monochromatic moving image formed at a predetermined frame rate using near-infrared light. The photographed image may be, for example, a color image captured by flashing visible light or a monochromatic still image captured using near-infrared light or visible light as illumination light. The retinal camera unit 2 may also capture other types of images such as fluorescein angiography images, indocyanine green fluorescent images and autofluorescent images.

The retinal camera unit 2 is provided with a chin rest and forehead placement for supporting a subject's face. Moreover, the retinal camera unit 2 is provided with an illumination optical system 10 and imaging optical system 30. The illumination optical system 10 irradiates illumination light to the fundus Ef. The imaging optical system 30 guides fundus-reflected light of illumination light to imaging devices (CCD image sensors 35, 38 (sometimes referred to simply as CCD)).

An observation light source 11 of the illumination optical system 10 includes a halogen lamp, for example. Light (observation illumination light) output from the observation light source 11 is reflected by a reflection mirror 12 with a curved reflection surface, passes through a condenser lens 13 and becomes near-infrared light after passing through a visible cut filter 14. Further, the observation illumination light is once converged near an imaging light source 15, reflected by a mirror 16 and passes through relay lenses 17 and 18, diaphragm 19 and relay lens 20. Then, the observation illumination light is reflected on a peripheral part (region surrounding an aperture part) of an aperture mirror 21, transmitted through a dichroic mirror 46 and refracted by an objective lens 22, thereby illuminating the fundus Ef. LED (Light Emitting Diode) may be used as the observation light source.

The fundus-reflected light of the observation illumination light is refracted by the objective lens 22, transmitted through the dichroic mirror 46, passes through the aperture part formed in the center region of the aperture mirror 21, transmitted through a dichroic mirror 55, travels through a focusing lens 31 and reflected by a mirror 32. Further, the fundus-reflected light is transmitted through a half-mirror 39A, reflected by a dichroic mirror 33 and forms an image on a light-receiving surface of the CCD 35 by a condenser lens 34. The CCD 35 detects the fundus-reflected light at a preset frame rate, for example. An image (observation image) based on the fundus-reflected light detected by the CCD 35 is displayed on a display device 3. When the imaging optical system 30 is focused on an anterior eye part, the observation image of the anterior eye part of the eye E is displayed.

The imaging light source 15 includes a xenon lamp, for example. Light (imaging illumination light) output from the imaging light source 15 is irradiated to the fundus Ef through the same route as the observation illumination light. The fundus-reflected light of the imaging illumination light is guided to the dichroic mirror 33 via the same route as the observation illumination light, transmitted through the dichroic mirror 33, reflected by a mirror 36 and forms an image on the light-receiving surface of the CCD 38 by a condenser lens 37. An image (photographed image) based on the fundus-reflected light detected by the CCD 38 is displayed on the display device 3. The display device 3 for displaying observation image and display device 3 for displaying photographed image may be the same or different. When similar photography is carried out by illuminating the eye E with infrared light, infrared photographed image is displayed. LED may be used as the imaging light source.

An LCD (Liquid Crystal Display) 39 displays fixation targets, targets for visual-acuity measurement, etc. The fixation target is a visual target (index) for fixating the eye E and used in fundus photography, OCT, etc.

Part of light output from the LCD 39 is reflected by the half-mirror 39A, reflected by the mirror 32, travels through the focusing lens 31 and dichroic mirror 55, passes through the aperture part of the aperture mirror 21, transmitted through the dichroic mirror 46, refracted by the objective lens 22, and projected onto the fundus Ef.

By changing a display position of the fixation target on the LCD 39's screen, a fixation position of the eye E may be changed. Examples of fixation positions of the eye E include position for acquiring a macula-centered image, position for acquiring optic-papilla-centered image, position for acquiring fundus-center image (centered at a location between macula and optic papilla), etc., as in conventional retinal cameras. Display positions of fixation targets may be changed arbitrarily.

As with conventional retinal cameras, the retinal camera unit 2 includes an alignment optical system 50 and focus optical system 60. The alignment optical system 50 generates a target (index, alignment target) for matching the position of the optical system to the eye E (that is, for performing alignment). The focus optical system 60 generates a target (index, split target) for focusing on the fundus Ef.

Light (alignment light) output from an LED 51 of the alignment optical system 50 passes through diaphragms 52 and 53 and relay lens 54, is reflected by the dichroic mirror 55, passes through the aperture part of the aperture mirror 21, is transmitted through the dichroic mirror 46 and is projected on the cornea of the eye E by the objective lens 22.

Cornea-reflected light of the alignment light passes through the objective lens 22, dichroic mirror 46 and aperture part, and then part of the cornea-reflected light is transmitted through the dichroic mirror 55, passes through the focusing lens 31, reflected by the mirror 32, transmitted through the half-mirror 39A, reflected by the dichroic mirror 33, and projected on the light-receiving surface of the CCD 35 by the condenser lens 34. An image (alignment target, alignment index) captured by the CCD 35 is displayed on the display device 3 together with observation image. The user conducts alignment by performing operations as with conventional retinal cameras. Alignment may be performed in a way in which the arithmetic and control unit 200 analyzes position of alignment target and moves the optical system (automatic alignment).

In order to perform focus adjustment, reflection surface of a reflection rod 67 is obliquely disposed in an optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, is formed an image on the reflection surface of the reflection rod 67 by a condenser lens 66 and then is reflected. Further, the focus light passes through the relay lens 20, is reflected at the aperture mirror 21, is transmitted through the dichroic mirror 46, is refracted by the objective lens 22 and is projected onto the fundus Ef.

Fundus-reflected light of the focus light passes through the same route as the cornea-reflected light of the alignment light and is detected by the CCD 35. An image (split target, split index) captured by the CCD 35 is displayed on the display device 3 together with observation image. The arithmetic and control unit 200, as in conventional technology, analyzes position of the split target and moves the focusing lens 31 and focus optical system 60 to perform focusing (automatic focusing). Focusing may be performed manually while observing split target.

The dichroic mirror 46 couples optical path for fundus photography and optical path for OCT. The dichroic mirror 46 reflects light of wavelength bands for OCT and transmits the light for fundus photography. The OCT optical path includes a collimator lens unit 40, optical-path-length changing part 41, galvano scanner 42, focusing lens 43, mirror 44 and relay lens 45. Members arranged in the OCT optical path and members included in the OCT unit 100 compose an example of an "optical system".

The collimator lens unit 40 converts light (signal light LS) emitted from an optical fiber 107 into a parallel light flux. Further, the collimator lens unit 40 enters returned light of the signal light LS from the eye E into the optical fiber 107. The collimator lens unit 40 is provided with a numerical-aperture changing part 40A that varies a beam diameter of the parallel light flux to change a numerical aperture (NA) for OCT. The numerical-aperture changing part 40A may be configured as a unit including a plurality of lenses with different powers that are selectively locatable in the optical path, or a unit including one or more lenses that are movable in an optical-axis direction. Change in the beam diameter of the signal light LS causes change in the numerical aperture for OCT.

The optical-path-length changing part 41 is movable in the direction indicated by an arrow in FIG. 1 to change length of the OCT optical path. The change of optical path length may be used for correcting optical path length in accordance with axial length of the eye E, adjusting interference state, etc. The optical-path-length changing part 41 includes a corner cube and mechanism for moving the corner cube, for example.

The galvano scanner 42 changes travelling direction of light (signal light LS) guided along the OCT optical path. Accordingly, the fundus Ef is scanned by the signal light LS. The galvano scanner 42 includes a galvano mirror for x-direction scanning of signal light LS, galvano mirror for y-direction scanning, and mechanism for independently driving these. Thereby, the signal light LS may be scanned in arbitrary directions on the xy-plane.

The focusing lens 43 is movable in directions indicated by an arrow shown in FIG. 1 and changes focus position for OCT.

[OCT Unit]

An example of a configuration of the OCT unit 100 is explained while referring to FIG. 2. The OCT unit 100 is provided with an optical system for obtaining OCT images of the fundus Ef. This optical system includes a configuration similar to conventional Spectral Domain OCT apparatus. That is, this optical system is configured to split low-coherence light into signal light and reference light, superpose the signal light returned form the fundus Ef with the reference light having traveled through a reference optical path to generate interference light, and detect spectral components of the interference light. The result of the detection (detection signal) is transmitted to the arithmetic and control unit 200.

When Swept Source OCT is applied, a wavelength-sweeping light source is provided instead of low-coherence light source while an optical member for spectrally decomposing interference light is not provided. In general, any known technology in accordance with OCT type may be arbitrarily applied for a configuration of the OCT unit 100.

A light source unit 101 outputs broadband, low-coherence light L0. The low-coherence light L0, for example, contains near-infrared wavelength band (about 800-900 nm) and has temporal coherence length of about tens of micrometer. It is possible to use wavelength bands invisible for human eyes such as near-infrared light having center wavelength of about 1040-1060 nm as the low-coherence light L0.

The light source unit 101 includes light-emitting device, such as SLD (super luminescent diode), LED, SOA (Semiconductor Optical Amplifier), etc.

The low-coherence light L0 output from the light source unit 101 is guided to a fiber coupler 103 through an optical fiber 102 and split into signal light LS and reference light LR.

The reference light LR is guided to an optical attenuator 105 through an optical fiber 104. Using any known technology, the arithmetic and control unit 200 controls the optical attenuator 105 for automatically adjusting light quantity (light intensity) of the reference light LR guided through the optical fiber 104. The reference light LR whose light quantity has been adjusted by the optical attenuator 105 is guided through the optical fiber 104 and reaches a polarization controller 106. The polarization controller 106 applies stress from outside to the optical fiber 104 of loop-form to adjust polarization states of the reference light LR being guided in the optical fiber 104, for example. Configuration of the polarization controller 106 is not limited to this and arbitrary known technology may be applied. The reference light LR whose polarization state has been adjusted by the polarization controller 106 is guided to an optical coupler 109.

The signal light LS generated by the fiber coupler 103 is guided through the optical fiber 107 and converted into a parallel light flux by the collimator lens unit 40. Further, the signal light LS travels through the optical-path-length changing part 41, galvano scanner 42, focusing lens 43, mirror 44 and relay lens 45, and reaches the dichroic mirror 46. Further, the signal light LS is reflected by the dichroic mirror 46, refracted by the objective lens and projected onto the fundus Ef. The signal light LS is scattered (reflected) at various depth positions of the fundus Ef. Back-scattered light (returned light) of the signal light LS from the fundus Ef travels along the same route as the outward way in the opposite direction to the fiber coupler 103, and reaches the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Further, the interference light LC is converted into a parallel light flux by a collimator lens 112, spectrally divided (spectrally decomposed) by a diffraction grating 113, converged by a condenser lens 114, and projected onto light-receiving surface of a CCD (image sensor) 115. Although the diffraction grating 113 shown in FIG. 2 is of transmission type, any other kinds of spectrally decomposing elements (such as reflection type) may be used.

The CCD 115 is for example a line sensor, detects the respective spectral components of spectrally-decomposed interference light LC and converts the components into electric charges. The CCD 115 accumulates the electric charges, generates detection signals and transmits the detection signals to the arithmetic and control unit 200.

Although Michelson-type interferometer is employed in the embodiment, any type of interferometer such as a Mach-Zehnder-type may be employed as necessary. Instead of CCD, other types of image sensors such as CMOS (Complementary Metal Oxide Semiconductor) may be used.

[Arithmetic and Control Unit]

A configuration of the arithmetic and control unit 200 is described. The arithmetic and control unit 200 analyzes detection signals input from the CCD 115 to form OCT images of the fundus Ef. Arithmetic processing for this may be the same as conventional Spectral Domain OCT apparatus.

The arithmetic and control unit 200 controls each part of the retinal camera unit 2, display device 3 and OCT unit 100. For example, the arithmetic and control unit 200 displays OCT images of the fundus Ef on the display device 3.

As controls of the retinal camera unit 2, the arithmetic and control unit 200 executes: action controls of the observation light source 101, imaging light source 103 and LED's 51 and 61; action control of the LCD 39; movement controls of the focusing lenses 31 and 43; movement control of the reflection rod 67; movement control of the focus optical system 60; action control of the numerical-aperture changing part 40A; movement control of the optical-path-length changing part 41; action control of the galvano scanner 42; etc.

As controls of the OCT unit 100, the arithmetic and control unit 200 executes: action control of the light source unit 101; action control of the optical attenuator 105; action control of the polarization controller 106; action control of the CCD 115; etc.

The arithmetic and control unit 200 includes a microprocessor, RAM, ROM, hard disk drive, communication interface, etc. as with conventional computers. Storage devices such as hard disk drive store computer programs for controlling the fundus observation apparatus 1. The arithmetic and control unit 200 may include various circuit boards such as circuit boards for OCT-image formation. The arithmetic and control unit 200 may include operation devices (input devices) such as a keyboard, mouse and/or display device such as LCD.

The retinal camera unit 2, display device 3, OCT unit 100 and arithmetic and control unit 200 may be integrally configured (that is, provided within a single case) or separately configured in two or more cases.

[Control System]

Figure 3:
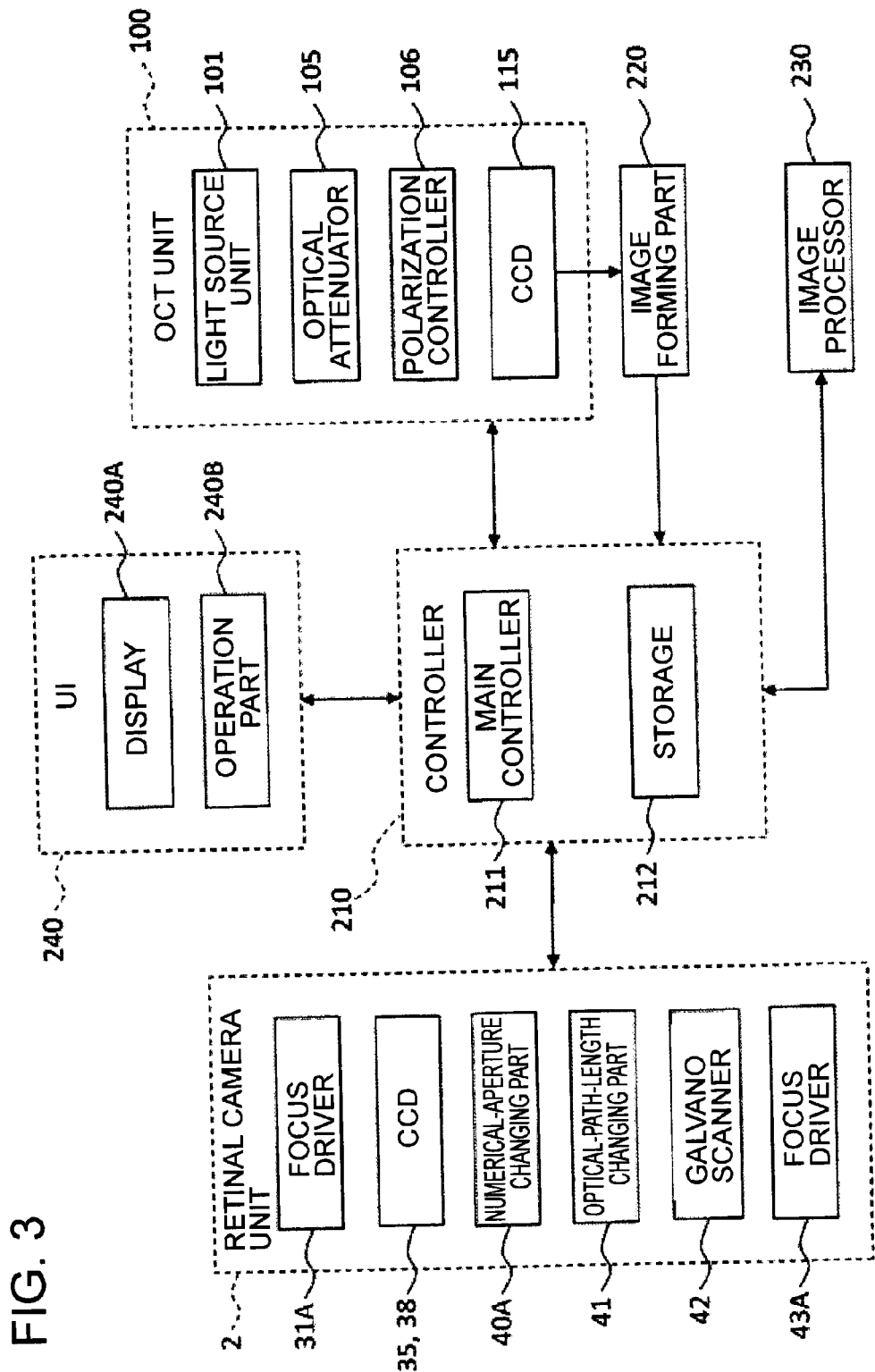
FIG. 3 is a schematic block diagram illustrating a configuration example of an optical image measuring apparatus (fundus observation apparatus) according to an embodiment.
Figure 4:
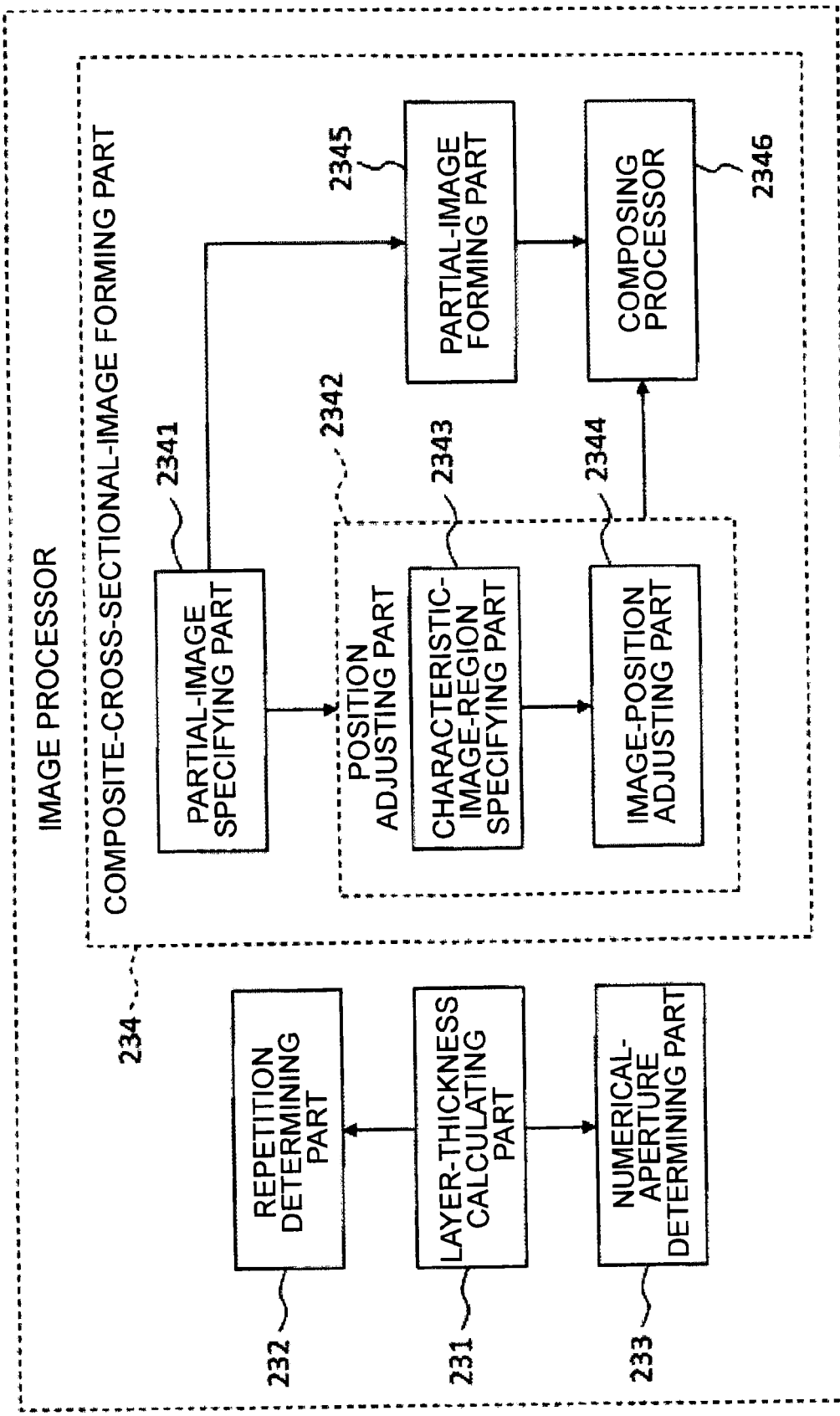
FIG. 4 is a schematic diagram illustrating a configuration example of an optical image measuring apparatus (fundus observation apparatus) according to an embodiment.

A configuration of a control system of the fundus observation apparatus 1 is described with reference to FIGS. 3 and 4.

(Controller)

A controller 210 is the center of the control system of the fundus observation apparatus 1. The controller 210 includes the above microprocessor, RAM, ROM, hard disk drive and communication interface, etc., for example. The controller 210 includes a main controller 211 and storage 212.

(Main Controller)

The main controller 211 performs various controls as described above. Specifically, the main controller 211 controls a focus driver 31A, numerical-aperture changing part 40A, optical-path-length changing part 41, galvano scanner 42 and focus driver 43A in the retinal camera unit 2. Also, the main controller 211 controls the light source unit 101, optical attenuator 105 and polarization controller 106 in the OCT unit 100.

The focus driver 31A moves the focusing lens 31 in an optical-axis direction. Accordingly, a focus position of the imaging optical system 30 is varied. The focus driver 43A moves the focusing lens 43 in along an optical axis under control of the main controller 211. Accordingly, a focus position of the OCT optical system is varied. This focus position regulates quantity of light of the signal light LS entering into the optical fiber 107 via the collimator lens unit 40. Therefore, an optimal focus position is realized by locating the focusing lens 43 at a position where a fiber end of the optical fiber 107 on the collimator lens unit 40 side is optically conjugate with the fundus Ef. Each of the focus drivers 31A and 43A includes an actuator such as a pulse motor and mechanism that transmits driving power generated by this actuator to the focusing lens 31 or 43.

The main controller 211 may be configured to control an optical-system driving mechanism (illustration omitted) to move the optical systems provided to the retinal camera unit 2 three-dimensionally. Such control is used for alignment and tracking. Tracking is an operation for moving optical system in accordance with eye movement of the eye E. When tracking is performed, alignment and focusing are performed in advance. Tracking is a function to maintain adequate positional relationship in which alignment and focusing are matched by causing position of optical system to follow eye movement.

The main controller 211 executes processing of writing data into the storage 212 and processing of reading out data from the storage 212.

(Storage)

The storage 212 stores various kinds of data. Data stored in the storage 212 may include OCT image data, fundus image data, eye information, etc., for example. The eye information includes information on subjects such as patient ID's, names and information on eyes such as identification of left/right eye. The storage 212 stores various programs and data for operating the fundus observation apparatus 1.

(Image Forming Part)

An image forming part 220 forms cross-sectional image data of the fundus Ef based on detection signals from the CCD 115. Like conventional Spectral Domain OCT, this processing includes noise elimination (noise reduction), filtering, dispersion compensation, FFT (Fast Fourier Transform), etc. For OCT apparatuses of other types, the image forming part 220 executes known processing in accordance with an applied type.

The image forming part 220 may include the aforementioned circuit boards, for example. "Image data" and an "image" based on this image data may be identified with each other in this specification.

(Image Processor)

An image processor 230 executes various image processing and analysis on images formed by the image forming part 220. For example, the image processor 230 executes various corrections such as brightness correction of images etc. Moreover, the image processor 230 executes various image processing and analysis on images obtained by the retinal camera unit 2 (fundus images, anterior eye part images, etc.).

The image processor 230 executes known image processing such as interpolation that interpolates pixels between cross-sectional images to form three-dimensional image data of the fundus Ef. Three-dimensional image data refers to image data whose pixel positions are defined by a three-dimensional coordinate system. Three-dimensional image data may be image data composed of three-dimensionally arranged voxels, for example. Such image data is referred to as volume data, voxel data, etc. For displaying an image based on volume data, the image processor 230 executes rendering processing (such as volume rendering, MIP (Maximum Intensity Projection), etc.) on the volume data to form image data of a pseudo three-dimensional image taken from a specific view direction. This pseudo three-dimensional image is displayed on a display device such as a display 240A.

It is also possible to form stack data of cross-sectional images as three-dimensional image data. Stack data is image data obtained by three-dimensionally arranging cross-sectional images acquired along scanning lines, wherein the arrangement is based on positional relationship of the scanning lines. That is, stack data is image data obtained by representing, with a three-dimensional coordinate system, cross-sectional images originally defined in respective two-dimensional coordinate systems (in other words, by embedding them into a three-dimensional space).

The image processor 230 includes a layer-thickness calculating part 231, repetition determining part 232, numerical-aperture determining part 233 and composite-cross-sectional-image forming part 234.

(Layer-Thickness Calculating Part)

The layer-thickness calculating part 231 analyzes a cross-sectional image of the fundus Ef to calculate thickness of a predetermined layer of the fundus Ef. This processing includes processing of specifying boundaries (upper and lower edges) of the predetermined layer of the fundus Ef and processing of finding the distance between the specified upper and lower edges.

The predetermined layer may be one or more layers of the fundus Ef to be observed. Layer tissues of the fundus Ef include a retina, choroid and sclera. The retina has a multi-layer structure including an inner limiting membrane, nerve fibre layer, ganglion cell layer, inner plexiform layer, inner nuclear layer, outer plexiform layer, outer nuclear layer, external limiting membrane, photoreceptor layer, and retinal pigment epithelium. The predetermined layer may be the retina, choroid or sclera, or one or more layer tissues included in the retina. The predetermined layer is set in advance. The predetermined layer may be set arbitrarily.

The processing of specifying the boundaries of the predetermined layer is processing generally called segmentation. The segmentation is image processing for specifying an image region in a cross-sectional image corresponding to a layer tissue of the fundus Ef. This processing is performed based on pixel values (brightness values) of the cross-sectional image. The respective layer tissues have characteristic reflectance and so image regions thereof have characteristic brightness values. The segmentation specifies a target image region based on such characteristic brightness values. Note that it may be configured to specify a surface of the fundus Ef (boundary between the retina and vitreous body) and specify a target image region based on distances from the positions of the surface.

After the boundaries (upper and lower edges) of the predetermined layer is specified, the layer-thickness calculating part 231, for example, counts the number of pixels between the upper and lower edges and finds the thickness of the predetermined layer based on the number of pixels. Information (layer-thickness information) indicating the thickness of the predetermined layer may be the number of pixels itself or distance information (conversion to distances in the real space, etc.) obtained from the number of pixels. Further, the layer-thickness information may be information indicating distribution of the thickness of the predetermined layer, or information obtained from this thickness distribution statistically (mean, mode, median, maximum, minimum, etc.). Further, the layer-thickness information may indicate thickness of the predetermined layer in a predetermined location (for example, a location on a line passing through the center of a frame).

(Repetition Determining Part)

The repetition determining part 232 determines the number of repetition of OCT scanning based on the layer-thickness information obtained by the layer-thickness calculating part 231. Although details will be explained later, OCT in the present embodiment performs scanning of the same site of the fundus Ef repeatedly while varying a focus position. The number of repetition determined by the repetition determining part 232 corresponds to the number of cross-sectional images acquired by OCT thus performed. When the focus position is changed stepwisely in such OCT, the number of repetition corresponds to the number of focus positions thus changed.

Figure 5:
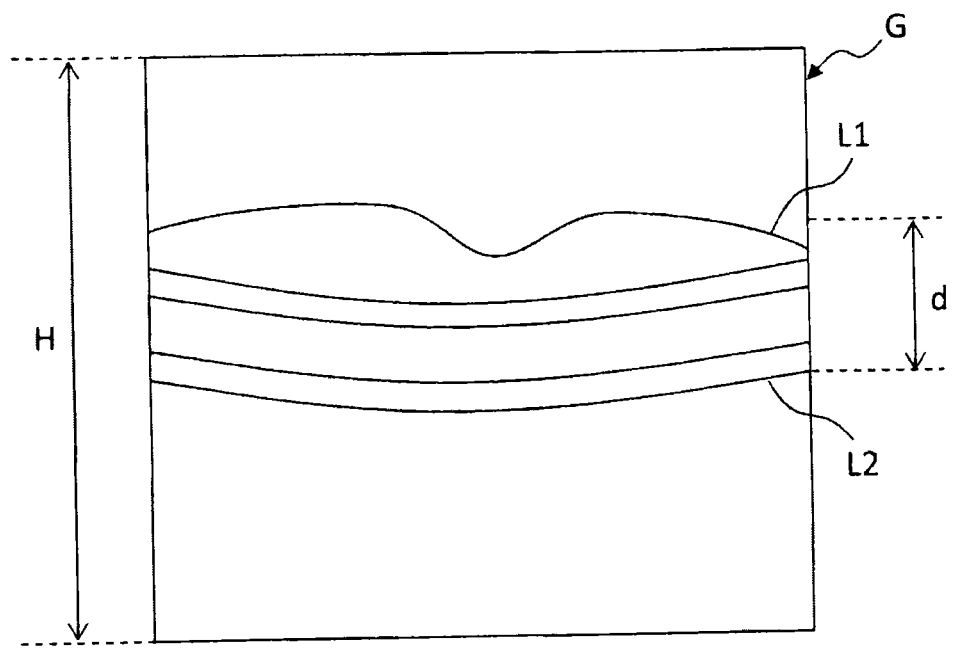
FIG. 5 is a schematic diagram for explaining a configuration of an optical image measuring apparatus (fundus observation apparatus) according to an embodiment.

Examples of processing of determining the number of repetition are described. As shown in FIG. 5, it is assumed that retinal thickness d is obtained as the layer-thickness information, wherein the retinal thickness d is distance between a retinal surface L1 (boundary between the inner limiting membrane and the vitreous body) and a retinal bottom L2 (boundary between the retinal pigment epithelium and the choroid). Further, the height of a frame of a cross-sectional image G (distance along the depth direction (z-direction) of the fundus Ef) is denoted by H.

A first example is described. The repetition determining part 232 divides the frame height H by the retinal thickness d. If the quotient H/d is an integer, the quotient H/d is set to be the number of repetition. On the other hand, if the quotient H/d is not an integer, the minimum value among integers larger than the quotient H/d is set to be the number of repetition.

A second example is described. The repetition determining part 232 finds a value d1 that is equal to or less than the retinal thickness d and is 1/(integer) of the frame height H: d1=d or d1<d and H/d1=(integer). This integer may be a maximum value that satisfies the above relationship or a smaller value than the maximum value. This integer value is used as the number of repetition.

A third example is described. The repetition determining part 232 arbitrarily sets a value d2 that is less than the retinal thickness d: d2<d. If the quotient H/d2 obtained by dividing the frame height H by the value d2 is an integer, the quotient H/d2 is set to be the number of repetition. On the other hand, if the quotient H/d2 is not an integer, the minimum value among integers larger than the quotient H/d2 is set to be the number of repetition. Here, the value d2 may be obtained by dividing the retinal thickness d by a predetermined value e: d2=d/e. Although substantially equivalent to this, it is possible to obtain the value d2 by multiplying the retinal thickness d by a predetermined ratio f (%):d2=d×f.

When "overlap width (margin for pasting together)" is used in processing of forming a composite cross-sectional image (described later), the number of repetition corresponding to the "overlap width" is added to the number of repetition obtained in the above processing examples. Further, the number of repetition may be determined based on the depth of focus as described later.

(Numerical-Aperture Determining Part)

As described above, the numerical aperture in OCT is varied by the numerical-aperture changing part 40A. The numerical-aperture determining part 233 determines a value of the numerical aperture so that the depth of focus (or the depth of field) in OCT becomes less than the thickness of the predetermined layer.

In general, the following relationship is known between the depth of focus D and the numerical aperture NA: $D=\lambda/(2\times NA^2)$. Here, $\lambda$ denotes a (center) wavelength of the signal light LS and is a fixed value.

In a case illustrated in FIG. 5, the numerical-aperture determining part 233 determines a value of the numerical aperture NA so that the depth of focus D becomes less than the retinal thickness d. More specifically, the numerical-aperture determining part 233 determines a value of the numerical aperture NA so that the following relationship is satisfied: $d>D=\lambda/(2\times NA^2)$, that is, $NA>\sqrt{(\lambda/2d)}$.

As a numerical example, when NA=0.088 and $\lambda$=840 nm, it will be obtained that D is approximately equal to 50 µm. Because the retinal thickness d is 200 to 300 µm in general, the depth of focus D<the retinal thickness d.

The number of repetition may be determined based on the depth of focus D thus obtained. For example, the numerical-aperture determining part 233 divides the frame height H by the depth of focus D. When the quotient H/D is an integer, the quotient H/D is set to be the number of repetition. On the other hand, if the quotient H/D is not an integer, the minimum value among integers larger than the quotient H/D is set to be the number of repetition, for example.

(Composite-Cross-Sectional-Image Forming Part)

In OCT measurements of the present embodiment, the same site of the fundus Ef is repeatedly scanned while varying the focus position. With this, cross-sectional images with different focus positions are acquired for this scanned site, wherein the number of the cross-sectional images corresponds to the number of repetition. The composite-cross-sectional-image forming part 234 forms one composite cross-sectional image based on two or more cross-sectional images thus acquired.

In order to perform such processing, the composite-cross-sectional-image forming part 234 includes a partial-image specifying part 2341, position adjusting part 2342, partial-image forming part 2345 and composing processor 2346. Further, the position adjusting part 2342 includes a characteristic-image-region specifying part 2343 and image-position adjusting part 2344.

(Partial-Image Specifying Part)

As described above, the same site of the fundus Ef is repeatedly scanned while varying the focus position in the present embodiment. Therefore, cross-sectional images correspond to different focus positions from each other. The partial-image specifying part 2341 specifies a partial image including an image region corresponding to a corresponding focus position. The image region corresponding to a focus position indicates a depth position (z-coordinate) of a frame corresponding to the concerned focus position.

Figure 6:
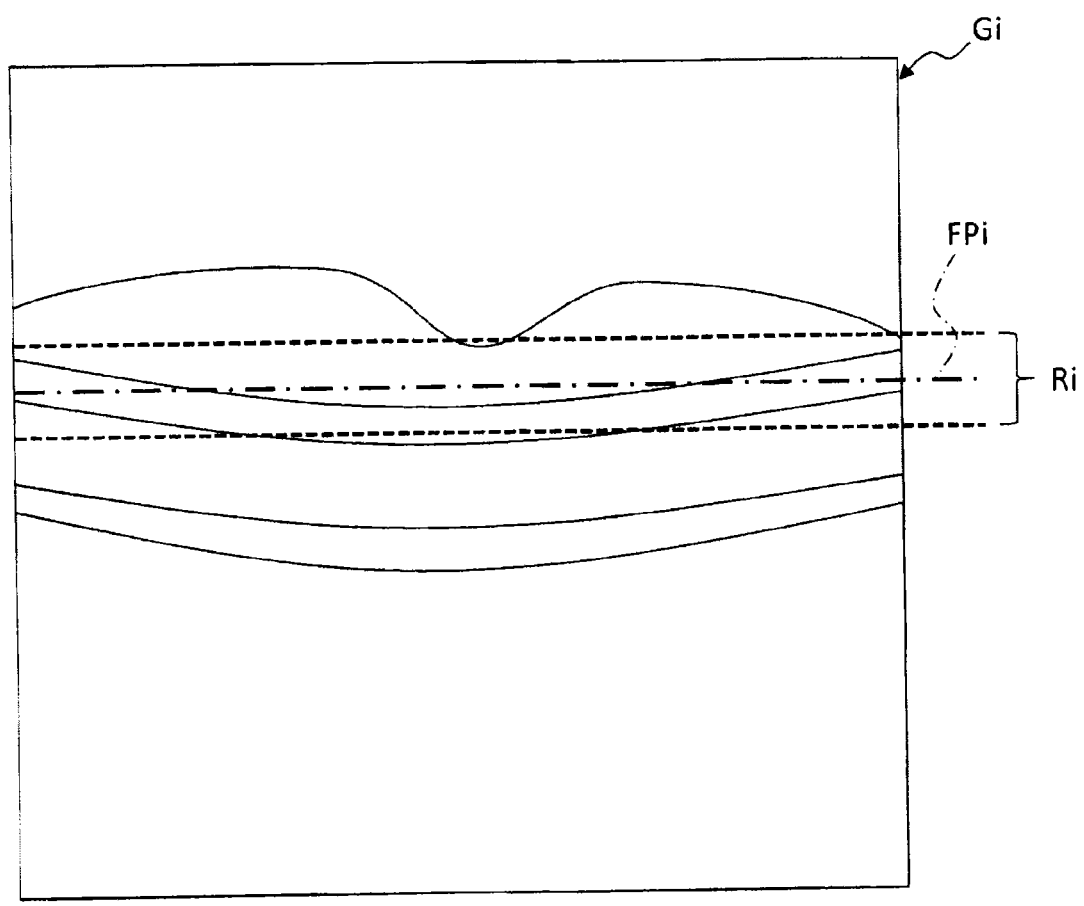
FIG. 6 is a schematic diagram for explaining a configuration of an optical image measuring apparatus (fundus observation apparatus) according to an embodiment.

Examples of processing of specifying a partial image are described. FIG. 6 illustrates one of the plurality of cross-sectional images acquired by the repetitive scanning. A line FPi indicates a focus position when a cross-sectional image Gi is acquired. Pixels located on the line FPi forms an image region corresponding to this focus position. The partial-image specifying part 2341 specifies an area Ri that extends from the image region formed by the pixels located on the line FPi to both +z-direction and −z-direction by the same distance, for example. An image region formed by the pixels included in the area Ri is set to be a partial region of the cross-sectional image Gi.

The area Ri may have a width (distance) obtained by dividing the frame height of the cross-sectional image Gi by the number of repetition described above, for example. This distance corresponds to the depth of focus described above, for example. When "overlap width" is used in composition processing (described later), the area Ri may include distance corresponding to the "overlap width".

(Position Adjusting Part)

The position adjusting part 2342 analyzes partial images specified by the partial-image specifying part 2341 to adjust relative positions between these partial images. In order to perform this processing, the position adjusting part 2342 includes the characteristic-image-region specifying part 2343 and image-position adjusting part 2344, for example.

(Characteristic-Image-Region Specifying Part)

The characteristic-image-region specifying part 2343 analyzes each of the partial images specified by the partial-image specifying part 2341 to specify a characteristic image region corresponding to a characteristic site of the fundus Ef. The characteristic site may be a macula (central fovea), optic disc, lesion site, etc. The characteristic image region may be an image region corresponding to a predetermined layer tissue(s). Processing of specifying a characteristic image region may be performed by, for example, specifying a predetermined image region in the same way as the layer-thickness calculating part 231, and specifying the characteristic image region based on the shape of the specified image region.

As a specific example, when a characteristic image region corresponding to a macula (central fovea) is to be specified, a characteristic depression (concavity) of the macula may be detected. When a characteristic image region corresponding to an optic disc is to be specified, a characteristic slope in the depth direction (z-direction) of the optic disc may be detected. When a characteristic image region corresponding to an edema (lesion site) is to be specified, a characteristic protrusion of the edema is detected. Alternatively, a cavity corresponding to the edema may be detected.

(Image-Position Adjusting Part)

The image-position adjusting part 2344 adjusts relative positions between the plurality of partial images specified by the partial-image specifying part 2341 based on the characteristic image regions specified by the characteristic-image-region specifying part 2343. This processing is position matching (registration) of adjacent partial images such that the characteristic image regions coincide with each other, for example. When "overlap width" is provided, the position matching of adjacent partial images may be performed so that the characteristic image regions overlap with each other. When "overlap width" is not provided, the position matching of adjacent partial images may be performed so that the characteristic image regions are smoothly connected.

(Partial-Image Forming Part)

The partial-image forming part 2345 trims cross-sectional images acquired by the repetitive scanning to form partial images. This trimming processing extracts pixel information (pixel positions and pixel values) of pixels located in the areas in the cross-sectional images specified by the partial-image specifying part 2341, for example.

(Composing Processor)

The composing processor 2346 composes the plurality of partial images formed by the partial-image forming part 2345 to form one cross-sectional image (composite cross-sectional image). In this composition processing, the pixel information of the plurality of partial images may be treated as one image data, for example. The composite cross-sectional image is an image representing a cross-section of the fundus Ef to which the repetitive scanning has been applied. Further, because each of the partial images includes an image region corresponding to a focus position for corresponding OCT scanning, the composite cross-sectional image is an image globally in focus.

Figure 7B:
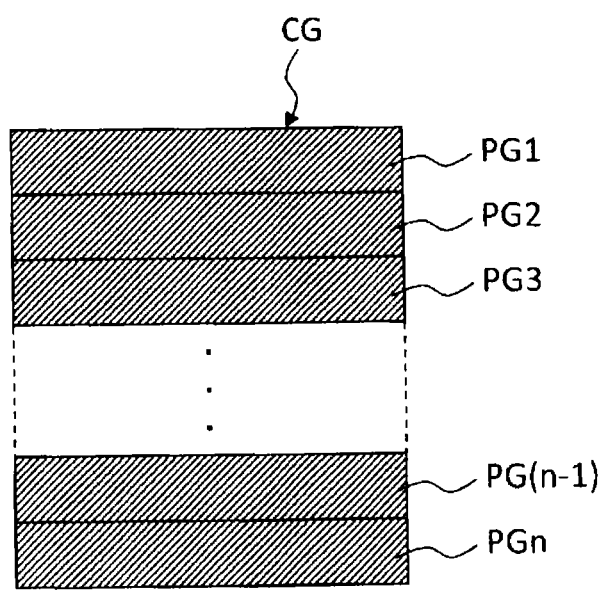
FIG. 7B is a schematic diagram for explaining a configuration of an optical image measuring apparatus (fundus observation apparatus) according to an embodiment.

Examples of composition processing of the present embodiment are described while referring to FIGS. 7A and 7B. The composition processing composes partial images PG1 to PGn of a plurality of cross-sectional images G1 to Gn illustrated in FIG. 7A. The partial images PG1 to PGn are images corresponding to the areas Ri of the cross-sectional images Gi illustrated in FIG. 6, respectively. In the present embodiment, the focus position for the repetitive scanning is changed stepwisely. In this case, as shown in FIGS. 6 and 7A, rectangular partial regions PG1 to PGn may be used. The composing processor 2346 composes the rectangular partial regions PG1 to PGn to form a composite cross-sectional image CG illustrated in FIG. 7B. The composite cross-sectional image CG is formed by arranging the rectangular partial regions PG1 to PGn in the depth direction (z-direction).

The composing processor 2346 may compose partial images based on the result of adjustment of relative positions between the partial images performed by the position adjusting part 2342 to form a composite cross-sectional image. Here, the result of position adjustment may be utilized each time or in accordance with the situation. As an example of the latter, it is possible to find misregistration of partial images based on displacements of characteristic image regions, and utilize the result of the position adjustment to perform the composition processing only if the misregistration is equal to or larger than a threshold.

The image processor 230 that functions as above includes, for example, the aforementioned microprocessor, RAM, ROM, hard disk drive, circuit boards, etc. Computer programs causing the microprocessor to execute the above functions are stored in storage devices such as the hard disk drive in advance.

(User Interface)

A user interface 240 includes the display 240A and operation part 240B. The display 240A includes a display device in the arithmetic and control unit 200 and/or display device 3. The operation part 240B includes operation devices in the arithmetic and control unit 200. The operation part 240B may include various buttons, keys, etc. provided on cases of the fundus observation apparatus 1 or outside thereof. For example, when the retinal camera unit 2 has a case similar to conventional retinal cameras, a joy stick, operation panel, etc. provided on this case may be included in the operation part 240B. The display 240A may include various display devices such as a touch panel etc. provided on the case of the retinal camera unit 2.

The display 240A and operation part 240B are not necessarily separate components. For example, like a touch panel, a compound device of display and operation functions may be applied. In this case, the operation part 240B includes the touch panel and computer programs. Contents of operation to the operation part 240B are input into the controller 210 as electrical signals. Further, operations and/or information input may be performed by means of graphical user interface (GUI) displayed on the display 240A and operation part 240B.

[Signal Light Scanning and OCT Images]

Now, scanning of signal light LS and OCT images are explained.

Scanning modes of the signal light LS by the fundus observation apparatus 1 may include, for example, horizontal, vertical, crossed, radial, circular, concentric, helical scans, etc. Taking observation site of fundus, analysis mode (retinal thickness etc.), time required for scanning, density of scanning, etc. into account, these scanning modes are selectively used.

The horizontal scan is one for scanning signal light LS in the horizontal direction (x-direction). The horizontal scan includes a mode of scanning signal light LS along multiple scanning lines extending in the horizontal direction and arranged in the vertical direction (y-direction). In this mode, the interval between scanning lines may be set arbitrarily. By setting the interval between adjacent scanning lines to be sufficiently narrow, three-dimensional image may be formed (three-dimensional scan). The vertical scan is performed in a similar manner.

The crossed scan is one for scanning signal light LS along a cross-shape trajectory consisting of two linear trajectories (line trajectories) orthogonal to each other. The radial scan is one for scanning signal light LS along a radial trajectory consisting of multiple line trajectories arranged at predetermined angles. The crossed scan is an example of the radial scan.

The circular scan is one for scanning signal light LS along a circular trajectory. The concentric scan is one for scanning signal light LS along multiple circular trajectories arranged concentrically around a predetermined center position. The circular scan is an example of the concentric scan. The helical scan is one for scanning signal light LS along a helical trajectory while making the turning radius gradually smaller (or greater).

Since the galvano scanner 42 is configured to scan signal light LS in the directions orthogonal to each other, the galvano scanner 42 is capable of scanning signal light LS in the x and y-directions independently. Signal light LS may be scanned along an arbitrary trajectory on the xy-plane by simultaneously controlling the orientations of two galvano mirrors included in the galvano scanner 42. As a result, various scanning modes as described above may be realized.

By scanning signal light LS in the modes described as above, it is possible to obtain a cross-sectional image in a plane spanned by the direction along a scanning line (scanning trajectory) and the fundus depth direction (z-direction). Moreover, when the interval between scanning lines is narrow, a three-dimensional image may be obtained.

A region in the fundus Ef to be scanned by signal light LS as described above, that is, a region in the fundus Ef subject to OCT is referred to as a scanning region. A scanning region of three-dimensional scan is a rectangular region in which multiple horizontal scans are arranged. A scanning region of concentric scan is a disciform region surrounded by the trajectory of the circular scan with maximum diameter. A scanning region of radial scan is a disciform (or polygonal) region connecting ends of scanning lines.

[Operations]

Figure 8:
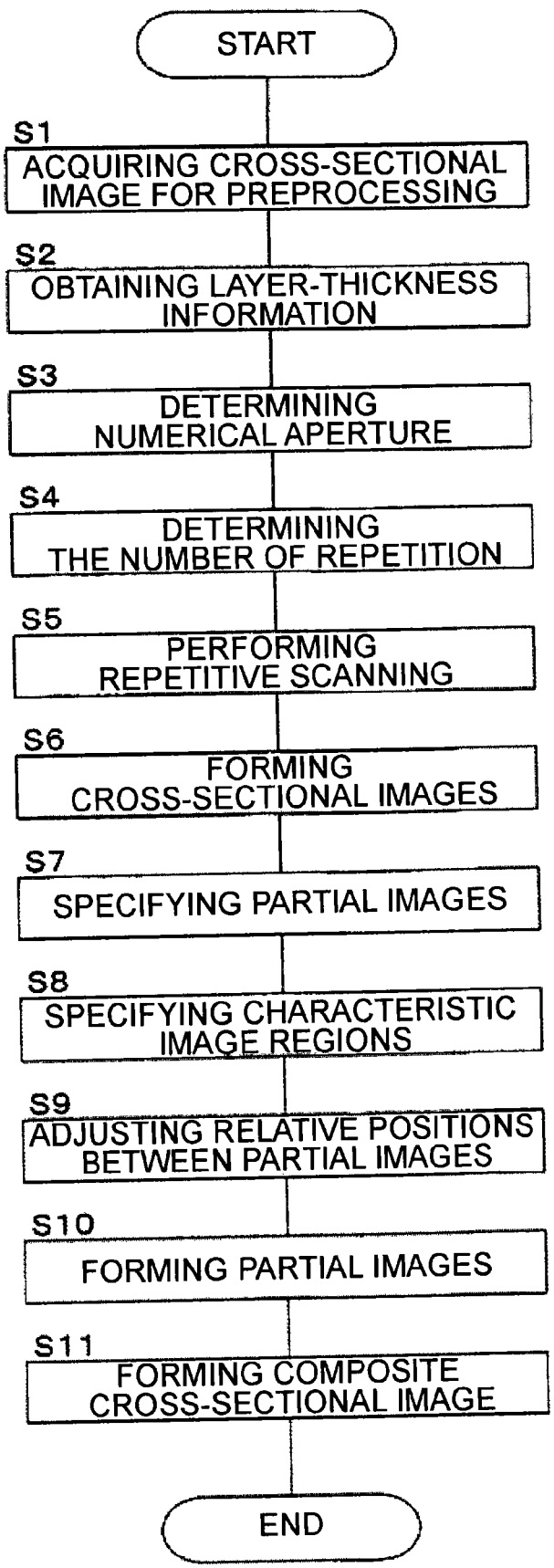
FIG. 8 is a flowchart representing an operation example of an optical image measuring apparatus (fundus observation apparatus) according to an embodiment.

Operations of the fundus observation apparatus 1 are described. FIG. 8 shows an example of an operation of the fundus observation apparatus 1. It is assumed that alignment and focusing have been performed already.

(S1: Acquiring Cross-Sectional Image for Preprocessing)

To begin with, a cross-sectional image for preprocessing is acquired. The preprocessing includes determination of the number of repetition of scanning, determination of numerical aperture, etc. The cross-sectional image acquired here is a live cross-sectional image acquired by scanning the same cross-section of the fundus Ef repeatedly, for example.

(S2: Obtaining Layer-Thickness Information)

The layer-thickness calculating part 231 analyzes the cross-sectional image acquired in Step S1 to obtain layer-thickness information indicating the thickness of a predetermined layer of the fundus Ef.

(S3: Determining Numerical Aperture)

The numerical-aperture determining part 233 determines a value of the numerical aperture so that the depth of focus becomes less than the thickness indicated in the layer-thickness information obtained in Step S2. The main controller 211 controls the numerical-aperture changing part 40A to set the numerical aperture to the determined value.

(S4: Determining the Number of Repetition)

The repetition determining part 232 determines the number of repetition in repetitive scanning of the signal light LS based on the layer thickness indicated in the layer-thickness information obtained in Step S2. Here, focus positions may also be determined. For example, the focus positions may be set to positions dividing the frame height of a cross-sectional image into N equal parts, wherein N represents the number of repetition.

(S5: Performing Repetitive Scanning)

Upon receiving a predetermined trigger, the main controller 211 performs repetitive scanning while changing focus positions. The repetitive scanning is performed with the numerical aperture set in Step S3 and by the times (the number of repetition) determined in Step S4. The number of the focus positions to be changed is equal to the number of repetition.

Figure 9:
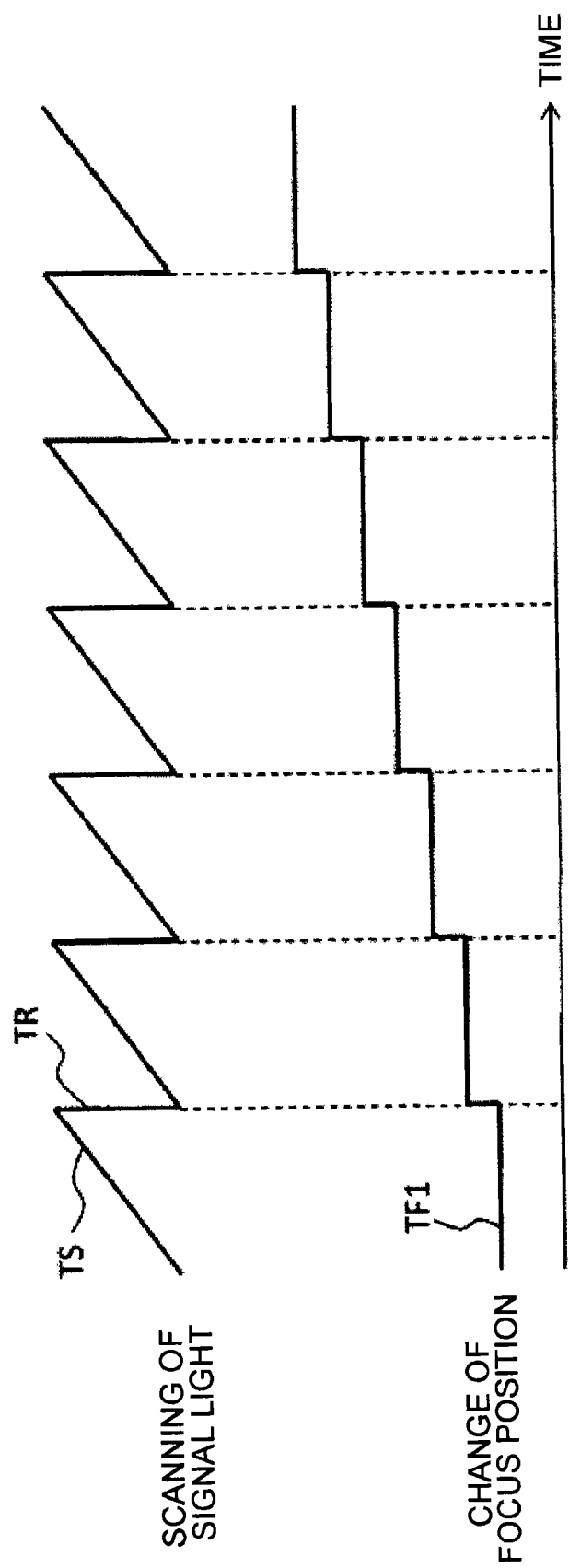
FIG. 9 is a timing chart for explaining an operation example of an optical image measuring apparatus (fundus observation apparatus) according to an embodiment.

The repetitive scanning may be controlled using a timing chart shown in FIG. 9, for example. For scanning of the signal light LS, an irradiation position of the signal light LS is changed in accordance with a saw-blade-shaped graph. A slant-line part TS of the graph indicates scanning action of the signal light LS with respect to different irradiation positions. A vertical part TR of the graph indicates an action that changes an irradiation position of the signal light LS from the last irradiation position among plurality of irradiation positions to the first irradiation position (returning action). On the other hand, the focus position is varied stepwisely as illustrated in a stepwise graph TF1. The change of focus position is performed simultaneously with the returning action of the irradiation position of the signal light LS (vertical part TR).

(S6: Forming Cross-Sectional Images)

The image forming part 220 forms a plurality of cross-sectional images based on data acquired by the repetitive scanning of Step S5. The number of the cross-sections formed here is equal to the number of repetition determined in Step S4. Each cross-sectional image is formed from data acquired during one slant-line part TS in the timing chart of scanning illustrated in FIG. 9.

(S7: Specifying Partial Images)

For each of the cross-sectional images formed in Step S6, the partial-image specifying part 2341 specifies a partial image including an image region corresponding to a corresponding focus position.

(S8: Specifying Characteristic Image Region)

The characteristic-image-region specifying part 2343 analyzes each of the partial images specified in Step S7 to specify a characteristic image region corresponding to a characteristic site of the fundus Ef.

(S9: Adjusting Relative Positions Between Partial Images)

The image-position adjusting part 2344 adjusts relative positions between the partial images based on the characteristic image regions specified in Step S8.

(S10: Forming Partial Images)

The partial-image forming part 2345 extracts the partial images specified in Step S7 from the cross-sectional images. With this, partial images are formed from the respective cross-sectional images. Note that processing of Step S10 may be performed at an arbitrary timing after Step S7.

(S11: Forming Composite Cross-Sectional Image)

The composing processor 2346 composes the partial images formed in Step S10 based on the results of adjustment of relative positions in Steps S9 to form a composite cross-sectional image of the fundus Ef. The composite cross-sectional image formed here is stored in the storage 212 by the main controller 211. The composite cross-sectional image may be displayed on the display 240A. Thus, this operation example ends.

[Actions and Effects]

Actions and effects of an optical image measuring apparatus of the present embodiment (fundus observation apparatus 1) are described.

The fundus observation apparatus 1 includes an optical system, image forming part, controller and composite-cross-sectional-image forming part. The optical system includes: a scanner (galvano scanner 42) configured to change an irradiation position of signal light on an object (fundus Ef); and a focus position changing part (focusing lens 43, focus driver 43A) configured to change focus position of the signal light. In addition, the optical system detects interference light of returned light of the respective signal light from the object and reference light. That is, the optical system performs OCT measurement of the object. The image forming part (220) forms a cross-sectional image based on detection results of a plurality of interference light corresponding to a plurality of irradiation positions of the signal light. The controller (main controller 211) controls the optical system to irradiate the signal light onto the plurality of irradiation positions repeatedly while changing the focus position. The composite-cross-sectional-image forming part (234) forms one composite cross-sectional image based on two or more cross-sectional images formed by the image forming part on the basis of results of repetitive irradiation of the signal light.

With such a configuration, a single cross-sectional image (composite cross-sectional image) is formed by composing a plurality of cross-sectional images acquired by scanning, a plurality of times, the same cross-section of the object while varying focus position, and therefore an image which is in-focus on the whole is obtained. Further, OCT may be performed by applying arbitrary settings of factors (such as numerical aperture) affecting lateral resolution. Accordingly, it is possible to acquire images with high lateral resolution and global sharpness.

The composite-cross-sectional-image forming part may include a partial-image specifying part (2341) configured to specify a partial image including an image region corresponding to a corresponding focus position for each of the cross-sectional images formed by the image forming part. In this case, the composite-cross-sectional-image forming part may compose two or more partial images thus specified to form the composite cross-sectional image. With this configuration, partial images including focus positions in cross-sectional images are composed, thereby capable of acquiring an image globally in-focus certainly and automatically.

The composite-cross-sectional-image forming part may include a position adjusting part (2342) configured to analyze the partial images specified by the partial-image specifying part to adjust relative positions between the partial images. In this case, the composite-cross-sectional-image forming part may compose the partial images whose relative positions have been adjusted to form the composite cross-sectional image. With this configuration, even when misregistration between cross-sectional images occurs due to eye movement, pulsation, etc. during repetitive scanning, this misregistration can be corrected to form the composite cross-sectional image.

The position adjusting part may include a characteristic-image-region specifying part (2343) configured to analyze each of the partial images to specify a characteristic image region corresponding to a characteristic site of the object. In this case, the position adjusting part (2342) may perform adjustment of the relative positions between the partial images based on specified characteristic image regions. With this configuration, it is possible to realize position adjustment with high precision and high accuracy based on the characteristic image regions.

The fundus observation apparatus (1) may include a repetition determining part (232) configured to determine the number of repetition in the repetitive irradiation of the signal light based on preobtained thickness of a predetermined layer of the object. With this configuration, the number of repetition in the repetitive scanning may be determined automatically. Further, the proper number of repetition may be derived by referring to the thickness of the predetermined layer.

The fundus observation apparatus (1) may include a layer-thickness calculating part (231) configured to analyze a cross-sectional image obtained prior to the repetitive irradiation of the signal light to calculate the thickness of the predetermined layer. With this configuration, the optimal number of repetition may be derived by actually measuring the object to obtain the thickness of the predetermined layer and referring to it.

The optical system may include a numerical-aperture changing part (40A) configured to change a numerical aperture, and a numerical-aperture determining part (233) configured to determine a value of the numerical aperture so that the depth of focus becomes less than the thickness of the predetermined layer may be provided. In this case, the controller may control the numerical-aperture changing part to set the numerical aperture to the determined value. With this configuration, it is capable of performing OCT measurement of the predetermined layer with high resolution and acquiring a composite cross-sectional image with high image quality. Incidentally, it is desired to determine the numerical aperture in consideration of an influence on lateral resolution as well.

The controller may change the focus position stepwisely for each repetition of irradiation of the signal light onto the plurality of irradiation positions when the repetitive irradiation of the signal light is performed (see FIG. 9). In this case, the composite-cross-sectional-image forming part may form the composite cross-sectional image based on rectangular partial images including image regions corresponding to the focus positions in the cross-sectional images. This configuration provides a concrete example of the repetitive scanning and the image composition processing.

The composite-cross-sectional-image forming part may include a partial-image forming part (2345) configured to trim each of the cross-sectional images to form partial images, and a composing processor (2346) configured to perform tiling processing of the partial images to form the composite cross-sectional image. Here, tiling is image composition processing for forming a single image by pasting a plurality of images together. The tiling in the present embodiment needs not employ "overlap width". This configuration provides one concrete example of the image composition processing.

MODIFICATION EXAMPLES

The configurations described above are merely illustrations for favorably implementing the present invention. Therefore, it is possible to make arbitrary modifications (omission, replacement, addition, etc.) without departing from the scope of the present invention. The followings are examples of such modifications. Note that components similar to the above embodiment are denoted by the same symbols.

Modification Example 1

As described above, misregistration between cross-sectional images occurs in a case in which eye movement, pulsation, body motion, etc. occur during repetitive scanning. When the misregistration is large, a plurality of cross-sectional images represents different cross-sections and therefore is unsuitable for formation of a composite cross-sectional image. The present modification example is used for solving such a problem.

Figure 10:
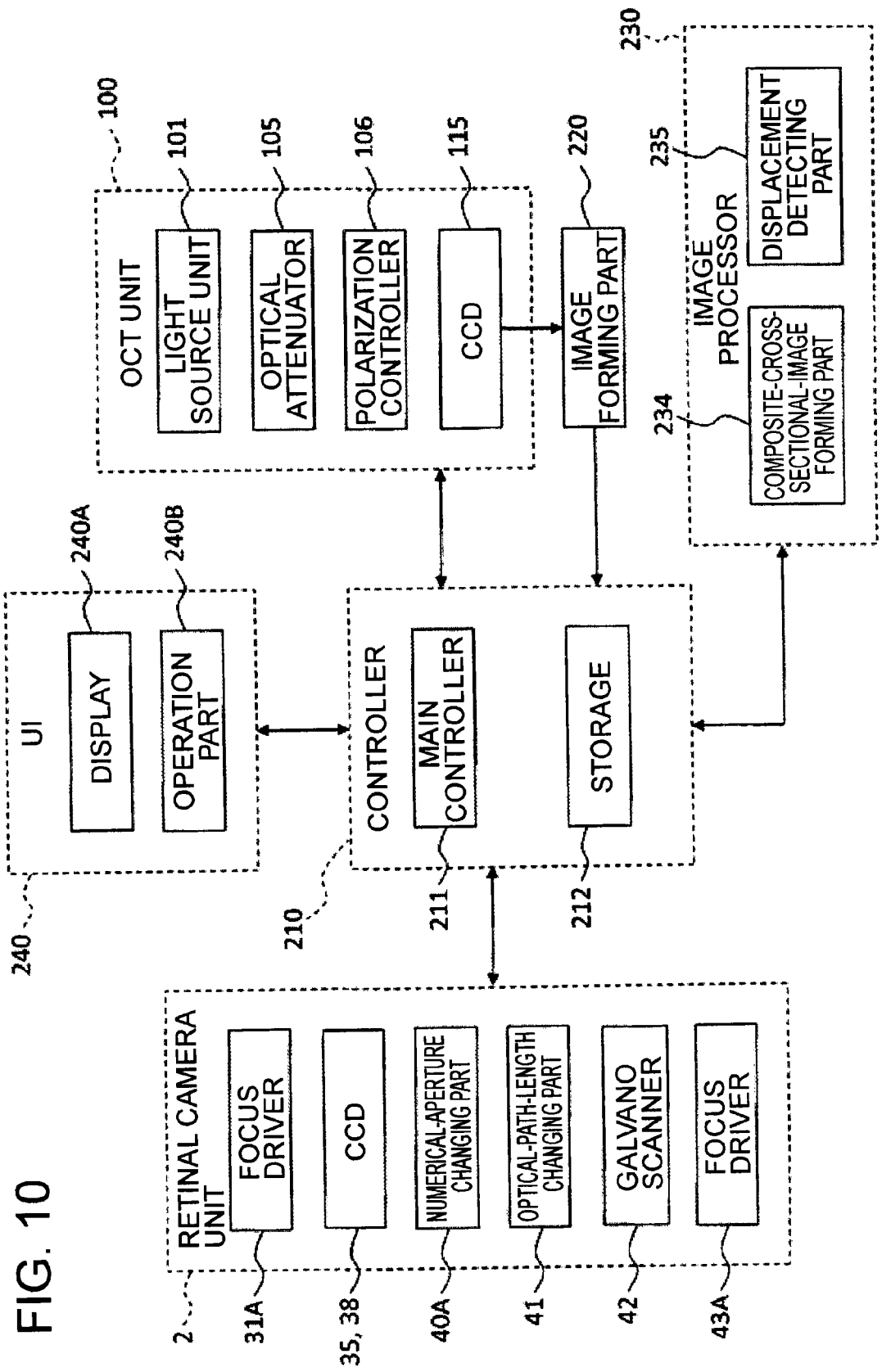
FIG. 10 is a schematic block diagram illustrating a configuration example of an optical image measuring apparatus (fundus observation apparatus) according to a modification.

FIG. 10 illustrates an example of the present modification example. An optical image measuring apparatus (fundus observation apparatus) of the present modification example has almost the same configurations as the above embodiment (see FIG. 3); however, it is different that the image processor 230 is provided with a displacement detecting part 235. Note that the image processor 230 of the present modification example may include at least one of the layer-thickness calculating part 231, repetition determining part 232 and numerical-aperture determining part 233 of the above embodiment. Further, the composite-cross-sectional-image forming part 234 of the present modification example may have configurations similar to/different from the above embodiment (see FIG. 4).

The displacement detecting part 235 detects a displacement between the OCT optical system and the object (fundus Ef) during the repetitive scanning. This displacement detection includes at least one of detection of displacement in the xy-direction and detection of displacement in the z-direction. It is desired that the displacement detection is performed prior to processing of forming a composite cross-sectional image.

The detection of displacement in the xy-direction may be performed, for example, by: acquiring an observation image of the fundus Ef (real-time infrared fundus image) concurrently with the repetitive scanning; and detecting chronological change of the position of a characteristic site of the fundus Ef in frames acquiring in chronological order. Alternatively, similar processing may be performed using an observation image of the anterior eye part of the eye E. Such processing may be performed in the tracking described above.

The detection of displacement in the xy-direction may be performed by analyzing a plurality of cross-sectional images acquired by the repetitive scanning. Note that these cross-sectional images are time-series (chronological) cross-sectional images whose frame rate corresponds to the repetition frequency of the repetitive scanning. The displacement in the xy-direction may be detected by detecting chronological change of the morphology (position (x-coordinate, y-coordinate), shape, size, etc.) of a characteristic site of the fundus Ef in the frames of the cross-sectional images.

The detection of displacement in the z-direction may be performed, for example, by analyzing a plurality of cross-sectional images acquired by the repetitive scanning. As an example, the displacement in the z-direction may be detected, as the detection of displacement in the xy-direction, by detecting chronological change of the position (z-coordinate) of a characteristic site of the fundus Ef in the frames of the cross-sectional images.

The main controller 211 performs new repetitive scanning of the fundus Ef based on the displacement detected by the displacement detecting part 235. In this processing, judgment whether or not new repetitive scanning is to be performed is carried out based on the detected displacement (such as a maximum value of displacement), for example. Further, this processing may include determination of control contents of the new repetitive scanning (scanning mode, scanning positions, etc.) on the basis of the detected displacement.

The new repetitive scanning is performed in the same scanning mode as the last time, for example. On the other hand, it is possible to apply a scanning mode different from the last time. As an example thereof, when horizontal scan is applied in the last new repetitive scanning, two horizontal scans adjacent to it may be applied as the new repetitive scanning, thereby reducing a risk of redoing.

The image forming part 220 forms a plurality of new cross-sectional images based on detection signals acquired by the newly performed repetitive scanning. The composite-cross-sectional-image forming part 234 forms a composite cross-sectional image based on the new cross-sectional images.

Displacement detection as described above may be performed on the plurality of new cross-sectional images formed by the image forming part 220. For example, it is possible to judge whether or not further repetitive scanning is to be performed based on the newly detected displacement. In this case, if the number of redoing of the repetitive scanning reaches a predetermined number, a message indicating this fact may be displayed on the display 240A.

According to the present modification example, new scanning may be performed based on the displacement between the optical system and the object during the repetitive scanning. For example, remeasurement may be automatically performed when the repetitive scanning is performed in an unsuitable way.

Modification Example 2

The present modification example solves the same problem as the Modification example 1. While the Modification example 1 performs new scanning based on displacement between the optical system and the object during the repetitive scanning, the present modification example performs notification based on the displacement.

A configuration of the present modification example may be the same as that of the Modification example 1 (see FIG. 10). As with the Modification example 1, the displacement detecting part 235 configured to detect a displacement between the OCT optical system and the object (fundus Ef) while performing the repetitive scanning.

The main controller 211 controls a notifying part to output notice information based on the displacement detected by the displacement detecting part 235. Examples of the notifying part include the display 240A, sound outputting part (not illustrated), etc. Types of the notice information depend on configurations of the notifying part, and examples thereof include visual information (character string information, image information, etc.), sound information (alarm messages, alarm signals, etc.), and the like.

The main controller 211 may calculate a statistic (maximum value, standard deviation, etc.) of the detected displacements and utilize the statistic for notification control. As an example thereof, if a statistic of the displacements is larger than a predetermined value, a message indicating this fact may be output. It is also possible to notify a statistic of the displacements itself. In these cases, a GUI may be displayed on the display 240A for the user to designate whether or not remeasurement is performed.

According to such a modification example, notification may be performed based on displacements between the optical system and the object during the repetitive scanning. Accordingly, it is possible to inform the user that the repetitive scanning has not been performed in a proper way, that remeasurement should be performed, and the like.

Modification Example 3

Figure 11:
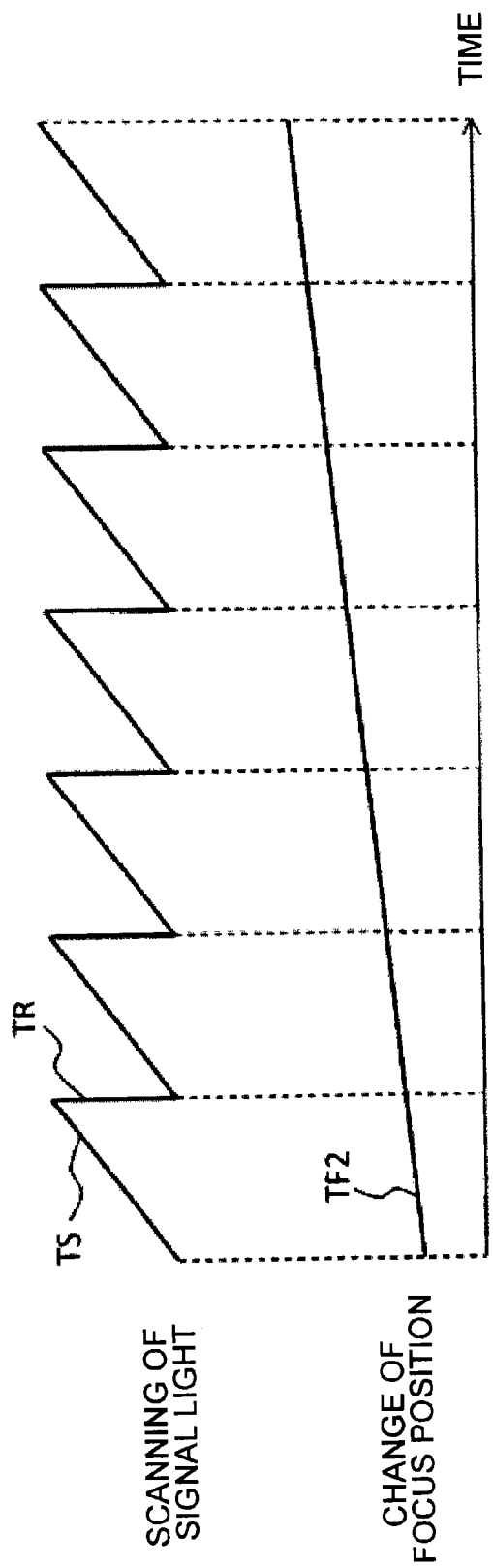
FIG. 11 is a timing chart for explaining an operation example of an optical image measuring apparatus (fundus observation apparatus) according to a modification.

The above embodiment changes focus positions stepwisely while performing repetitive scanning; however, aspects of changing focus positions are not so limited. For example, focus positions may be changed continuously during the repetitive scanning. FIG. 11 illustrates an example of a timing chart of such a case.

Scanning of the signal light LS is performed in the same way as the above embodiment. A slant-line part TS of the graph indicates scanning action of the signal light LS with respect to different irradiation positions. A vertical part TR of the graph indicates returning action of irradiation positions of the signal light LS. On the other hand, focus positions are changed continuously as shown by a linear graph TF2, which is different from the above embodiment.

When focus positions are changed stepwisely as in the above embodiment, the focus positions are the same for each repetition of scanning (that is, for each of the slant-line parts TS), and the each repetition corresponds to a single focus position. On the other hand, the present modification example varies focus positions continuously. Therefore, if the areas Ri of the cross-sectional images provided to the formation of a composite cross-sectional image are rectangular as shown in FIG. 6 in the above embodiment, there is a risk that focus positions deviate from the areas Ri. Further, if the areas Ri are set to be large so that focus positions do not deviate from them, portions far from focus positions go a bit out of focus.

Figure 12A:
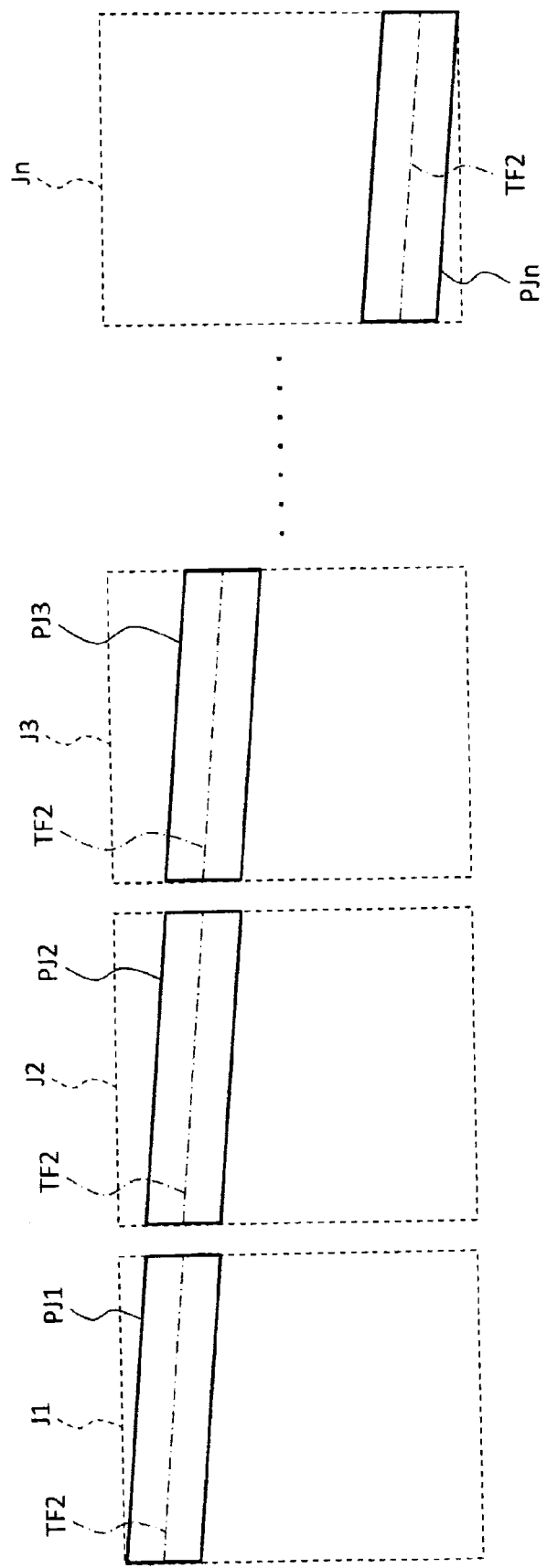
FIG. 12A is a schematic diagram for explaining an operation example of an optical image measuring apparatus (fundus observation apparatus) according to a modification.

Taking such situations into consideration, the present modification example utilizes parallelogram-shaped partial regions in cross-sectional images to form a composite cross-sectional image. FIG. 12A illustrates an example thereof. A plurality of cross-sectional images J1 to Jn illustrated in FIG. 12A are formed based on data acquired by repetitive scanning performed in accordance with the timing chart shown in FIG. 11. Here, each of the cross-sectional images Ji (i=1 to n) is formed from data acquired by scanning corresponding to the i-th slant-line part TS in the timing chart.

In this example, a partial image PJi of the cross-sectional image Ji is used for composition processing. Each of the partial images PJi is an image region having a width that extends from the graph TF2 (an image region corresponding to the graph TF2) of the focus position during the period of the corresponding slant-line part TS to both +z-direction and −z-direction by the same distance. Since the graph TF2 is a monotonic, linear graph (that is, a graph with a constant slope), each of the partial images PJi becomes a parallelogram-shaped image region. Each of the partial images PJi is an example of a parallelogram-shaped partial image.

Figure 12B:
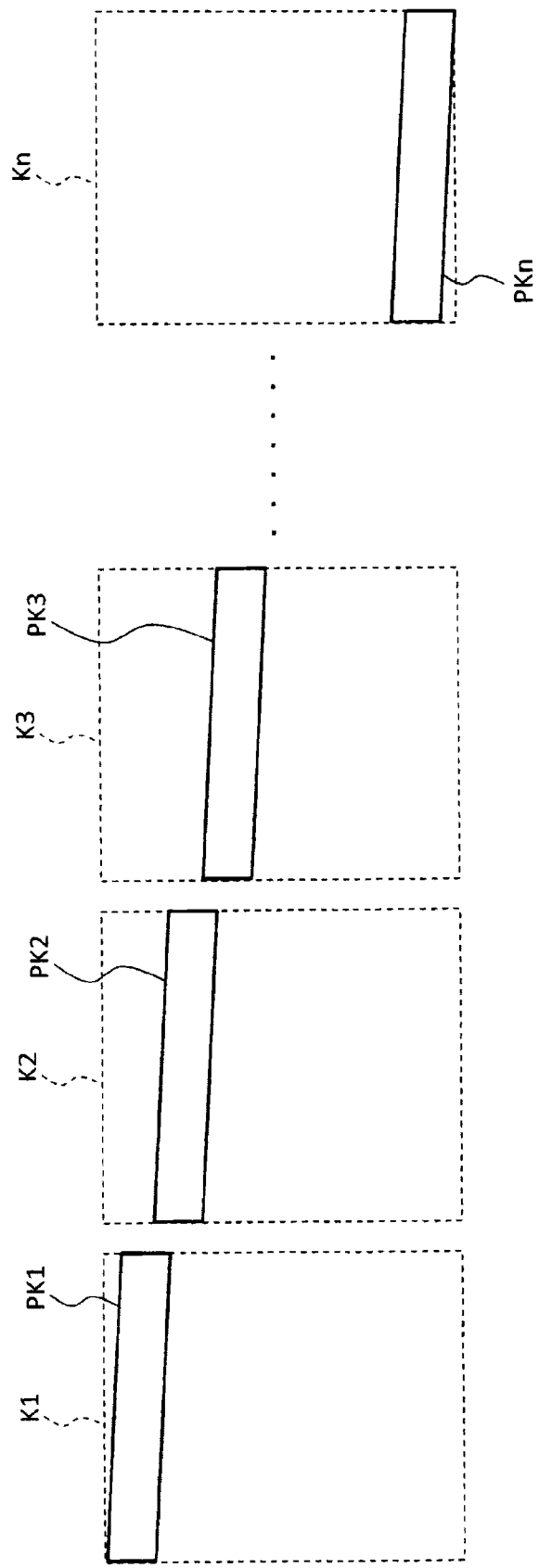
FIG. 12B is a schematic diagram for explaining an operation example of an optical image measuring apparatus (fundus observation apparatus) according to a modification.

The composite-cross-sectional-image forming part 234 composes such parallelogram-shaped partial images PJ1 to PJn to form a composite cross-sectional image. This composite cross-sectional image is obtained by arranging the parallelogram-shaped partial images PJ1 to PJn in the depth direction (z-direction) (illustration omitted). In the present example, each of the partial images PJi is provided with "overlap width", and composition is performed so that parts of adjacent partial images PJi, PJ(i+1) overlap with each other. It is also possible to perform composition processing without providing "overlap width" as in partial images PK1 to PKn of cross-sectional images K1 to Kn illustrated in FIG. 12B.

Regarding triangular regions at upper and lower edges of a frame of the composite cross-sectional image, it is possible to use images of triangular regions in cross-sectional images including partial images PJi closest to them (namely, cross-sectional images J1 and Jn). Alternatively, such images of the triangular regions may be obtained by extending the graph TF2 shown in FIG. 11 in the forward and backward chronologically.

Figure 13:
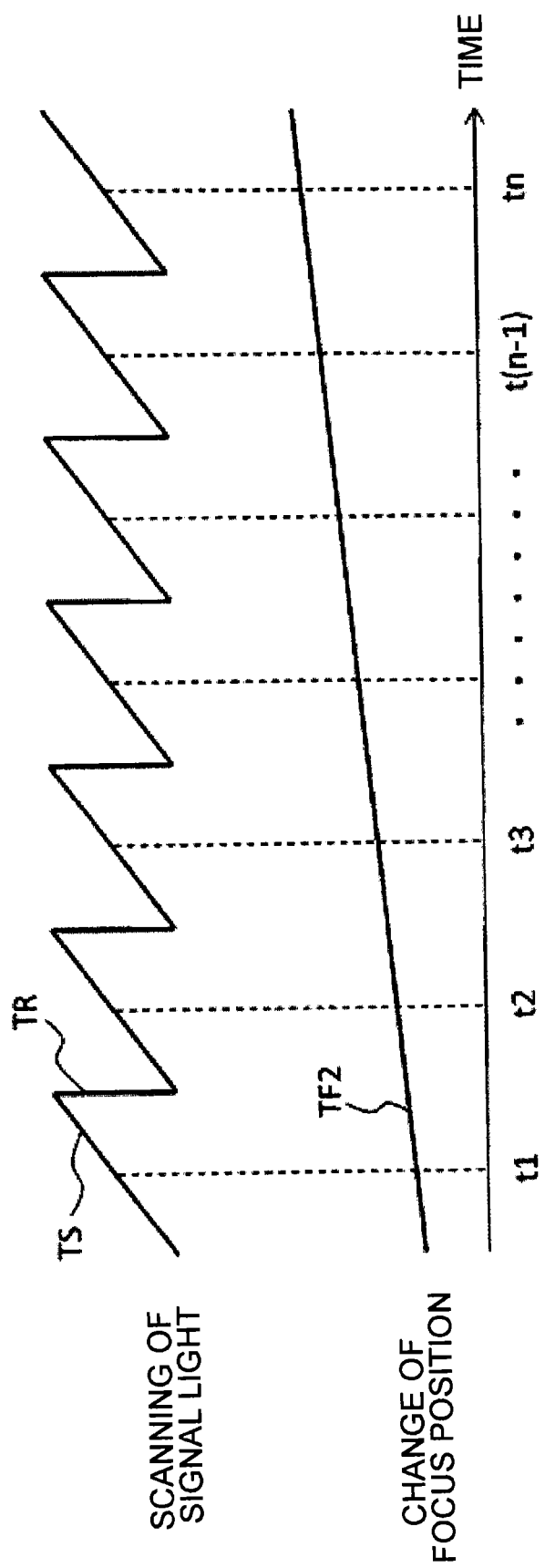
FIG. 13 is a timing chart for explaining an operation example of an optical image measuring apparatus (fundus observation apparatus) according to a modification.

FIG. 13 illustrates another example of the case in which focus position is changed continuously. In this example, composition processing is performed using rectangular partial images as in the above embodiment, and repetitive scanning is performed as focus position is changed continuously.

The main controller 211 is capable of recognizing focus position (z-coordinate) at any timing of the repetitive scanning because it executes control of focus positions. Alternatively, focus position may be recognized using a sensor that detects a position of the focusing lens 43 during the repetitive scanning.

The main controller 211 obtains a representative focus position in a period corresponding to the respective slant-line parts TS in scanning of the signal light LS. The representative focus positions may be focus positions at center points t1 to tn in the periods corresponding to the slant-line parts TS, for example.

The composite-cross-sectional-image forming part 234 specifies rectangular partial images so as to include image regions (consisting of pixels on line segments orthogonal to the z-direction) corresponding to representative focus positions corresponding to the slant-line parts TS for the respective cross-sectional images. Then, the composite-cross-sectional-image forming part 234 composes the specified rectangular partial images to form a composite cross-sectional image. It is also possible to set rectangular partial images so as to include image regions TF2 corresponding to focus positions illustrated in FIG. 12A.

The present modification example changes focus positions continuously, thereby being capable of simplifying a configuration and control of the focus driver 43A in comparison with the case of stepwise movement.

Modification Example 4

The above embodiment forms a composite cross-sectional image by trimming a plurality of cross-sectional images and pasting them together; however, composition processing is not so limited. For example, a composite cross-sectional image may be formed by superposing a plurality of cross-sectional images using a layer function.

Figure 14:
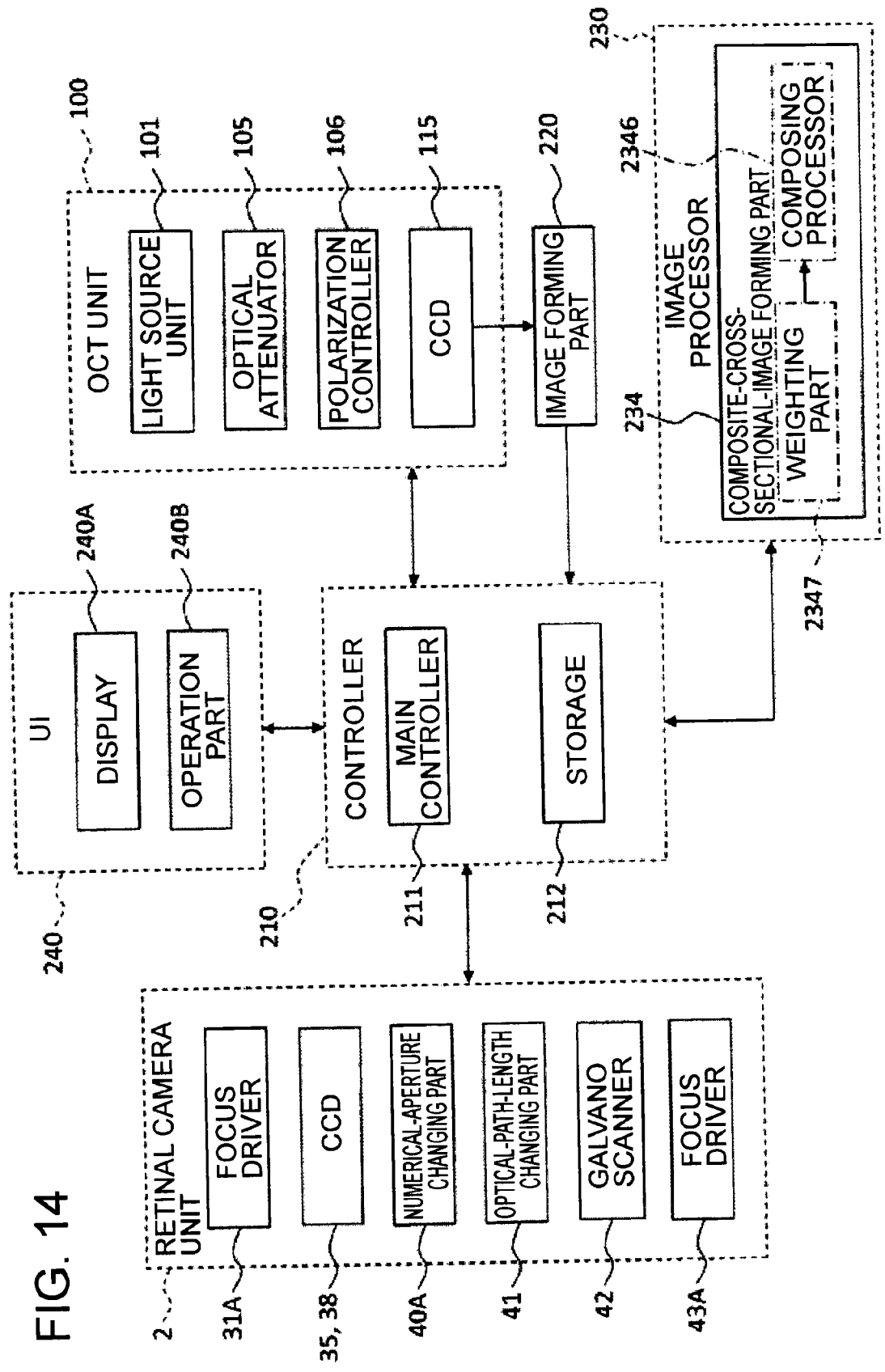
FIG. 14 is a schematic block diagram illustrating a configuration example of an optical image measuring apparatus (fundus observation apparatus) according to a modification.

FIG. 14 illustrates an example of a configuration of the present modification example. An optical image measuring apparatus (fundus observation apparatus) of the present modification example has almost the same configurations as the above embodiment (see FIG. 3); however, it is different that the image processor 230 is provided with a weighting part 237. Note that the image processor 230 of the present modification example may include at least one of the layer-thickness calculating part 231, repetition determining part 232 and numerical-aperture determining part 233 of the above embodiment. Further, the composite-cross-sectional-image forming part 234 of the present modification example may have configurations similar to/different from the above embodiment (see FIG. 4).

Figure 15B:
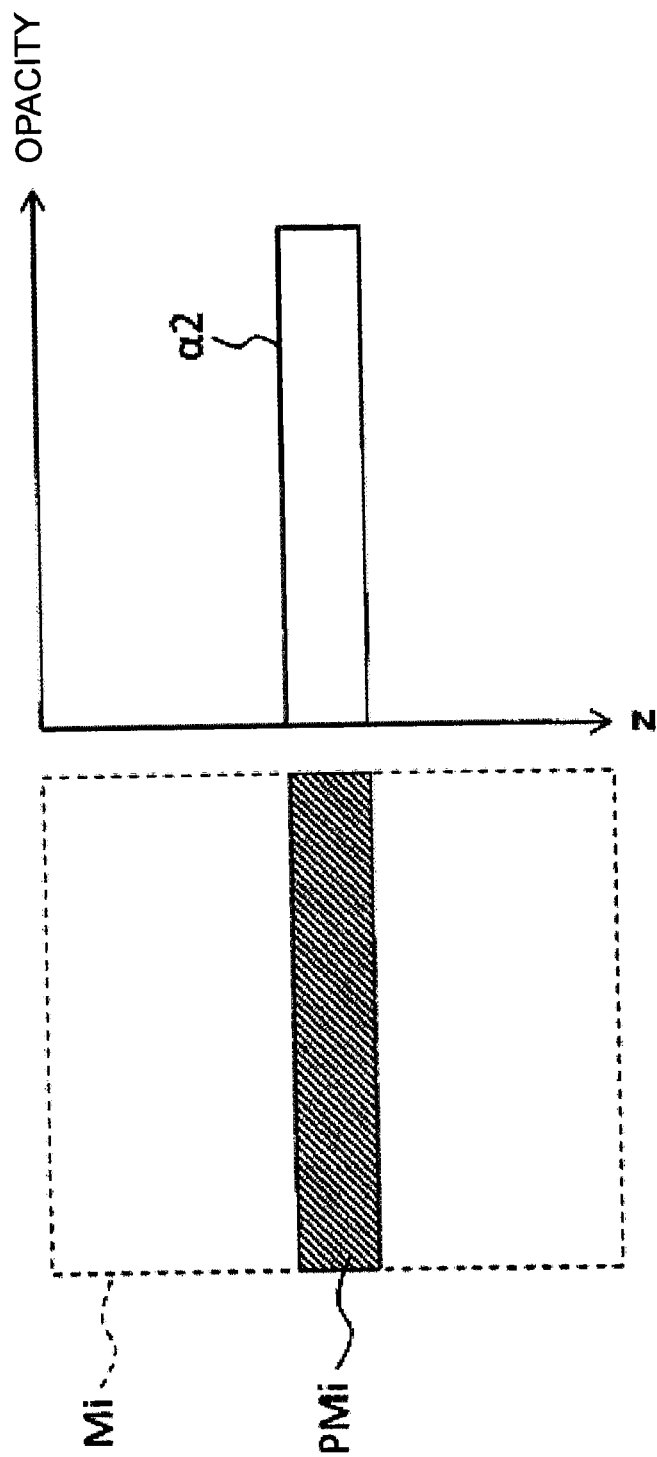
FIG. 15B is a schematic diagram for explaining an operation example of an optical image measuring apparatus (fundus observation apparatus) according to a modification.

The weighting part 237 performs weighting of pixels of each cross-sectional image to be provided to composition processing. The weighting may be performed by assigning transparency information (alpha values) to alpha channels of pixels of a cross-sectional image, for example. The weighting part 237 assigns the transparency information such that opacity of pixels constituting partial images in the above embodiment becomes relatively higher. FIGS. 15A and 15B illustrate concrete examples thereof.

It is assumed that a plurality of cross-sectional images Mi (i=1 to n) is acquired by repetitive scanning. An opacity graph α1 shown in FIG. 15A gives transparency information to alpha channels of pixels of cross-sectional images Mi so that opacity of pixels of partial images PMi in the cross-sectional images Mi becomes relatively higher. The cross-sectional images Mi to which the opacity graph α1 is applied are images in which opacity of the partial images PMi is high and opacity gradually becomes lower as the distance from the partial images PMi increases.

In an opacity graph α2 shown in FIG. 15B, opacity takes a maximum value in partial images PMi of the cross-sectional images Mi and takes a minimum value in other areas. The cross-sectional images Mi to which the opacity graph α2 is applied are images in which areas other than the partial images PMi are transparent.

The composite-cross-sectional-image forming part 234 superposes the cross-sectional images M1 to Mn whose pixels have been weighted by the weighting part 237 to form a composite cross-sectional image. If position matching is performed on the cross-sectional images M1 to Mn, the processing may be performed in the same way as in the above embodiment.

Other Modification Examples

In the above embodiments, the optical-path-length difference between optical paths of the signal light LS and reference light LR is changed by varying the position of the optical-path-length changing part 41; however, methods for changing the optical-path-length difference are not limited to this. For example, the optical-path-length difference may be changed by providing a reflection mirror (reference mirror) in the optical path of the reference light and moving the reference mirror in the advancing direction of the reference light to change the optical path length of the reference light. Further, the optical-path-length difference may be changed by moving the retinal camera unit 2 and/or OCT unit 100 relatively to the eye E to change the optical path length of the signal light LS. When an object is not a site of a living body or the like, the optical-path-length difference may be changed by moving the object in the depth direction (z-direction).

What is claimed is:

1. An optical image measuring apparatus comprising:
an optical system including a scanner configured to change an irradiation position of signal light on an object and a focus position changer configured to change focus position of the signal light, and configured to detect interference light of returned light of the respective signal light from the object and reference light;
an image forming part included within at least one processor including circuitry and configured to form a cross-sectional image based on detection results of a plurality of interference light corresponding to a plurality of irradiation positions of the signal light;
a programmed controller configured to control the optical system to irradiate the signal light onto the plurality of irradiation positions repeatedly while changing the focus position;
a composite-cross-sectional-image forming part included within the at least one processor including circuitry and configured to form one composite cross-sectional image based on two or more cross-sectional images formed by the image forming part on the basis of results of repetitive irradiation of the signal light, wherein
the programmed controller is further configured to change the focus position continuously when the repetitive irradiation of the signal light is performed, and
the composite-cross-sectional-image forming part is further configured to form the one composite cross-sectional image based on a parallelogram-shaped partial image including an image region corresponding to a corresponding focus position in each cross-sectional image.

2. The optical image measuring apparatus of claim 1, wherein the composite-cross-sectional-image forming part comprises a partial-image specifying part included within the at least one processor including circuitry and configured to specify a partial image including an image region corresponding to a corresponding focus position for each of the two or more cross-sectional images, and composes specified two or more partial images to form the composite cross-sectional image.

3. The optical image measuring apparatus of claim 2, wherein the composite-cross-sectional-image forming part comprises a position adjusting part included within the at least one processor including circuitry and configured to analyze the two or more partial images to adjust relative positions between the two or more partial images, and composes the two or more partial images whose relative positions have been adjusted to form the composite cross-sectional image.

4. The optical image measuring apparatus of claim 3, wherein the position adjusting part comprises a characteristic-image-region specifying part included within the at least one processor including circuitry and configured to analyze each of the two or more partial images to specify a characteristic image region corresponding to a characteristic site of the object, and adjusts the relative positions between the two or more partial images based on specified characteristic image regions.

5. The optical image measuring apparatus of claim 1, further comprising a displacement detecting part included within the at least one processor including circuitry and configured to detect a displacement between the optical system and the object during the repetitive irradiation of the signal light, wherein the programmed controller performs new repetitive irradiation of the signal light based on the detected displacement, and the composite-cross-sectional-image forming part forms the composite cross-sectional image based on two or more new cross-sectional images formed on the basis of results of the new repetitive irradiation of the signal light.

6. The optical image measuring apparatus of claim 1, further comprising a displacement detecting part included within the at least one processor including circuitry and configured to detect a displacement between the optical system and the object during the repetitive irradiation of the signal light, wherein the programmed controller controls a notifier to output notice information based on the detected displacement.

7. The optical image measuring apparatus of claim 1, further comprising a repetition determining part included within the at least one processor including circuitry and configured to determine the number of repetition in the repetitive irradiation of the signal light based on preobtained thickness of a predetermined layer of the object.

8. The optical image measuring apparatus of claim 7, further comprising a layer-thickness calculating part included within the at least one processor including circuitry and configured to analyze a cross-sectional image obtained prior to the repetitive irradiation of the signal light to calculate the thickness of the predetermined layer.

9. The optical image measuring apparatus of claim 7, wherein the optical system comprises a numerical-aperture changing part including a plurality of lenses with different powers that are selectively locatable in an optical path, or one or more lenses that are movable in an optical-axis direction and configured to change a numerical aperture, further comprising a numerical-aperture determining part included within the at least one processor including circuitry and configured to determine a value of the numerical aperture so that the depth of focus becomes less than the thickness of the predetermined layer, wherein the programmed controller controls the numerical-aperture changing part to set the numerical aperture to the determined value.

10. The optical image measuring apparatus of claim 1, wherein the programmed controller changes the focus position stepwisely for each repetition of irradiation of the signal light onto the plurality of irradiation positions when the repetitive irradiation of the signal light is performed, and the composite-cross-sectional-image forming part forms the composite cross-sectional image based on a rectangular partial image including an image region corresponding to a corresponding focus position in each cross-sectional image.

11. The optical image measuring apparatus of claim 1, wherein the composite-cross-sectional-image forming part comprises a partial-image forming part included within the at least one processor including circuitry and configured to trim each of the two or more cross-sectional images to form the partial image, and a composing processor configured to perform tiling processing of two or more partial images obtained from the two or more cross-sectional images to form the composite cross-sectional image.

12. The optical image measuring apparatus of claim 1, wherein the composite-cross-sectional-image forming part comprises a weighting part included within the at least one processor including circuitry and configured to perform weighting of pixels of each of the two or more cross-sectional images, and a composing processor configured to perform superposition processing of the two or more cross-sectional images with the weighted pixels to form the composite cross-sectional image.

* * * * *